United States Patent
Su et al.

(10) Patent No.: US 9,446,235 B2
(45) Date of Patent: Sep. 20, 2016

(54) LOW FREQUENCY ELECTRICAL STIMULATION THERAPY FOR PELVIC FLOOR DISORDERS

(71) Applicant: Medtronic, Inc., Minneapolis, MN (US)

(72) Inventors: Xin Su, Plymouth, MN (US); Dwight E. Nelson, Shoreview, MN (US); Timothy J. Ness, Birmingham, AL (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/210,981

(22) Filed: Mar. 14, 2014

(65) Prior Publication Data

US 2014/0277250 A1 Sep. 18, 2014

Related U.S. Application Data

(60) Provisional application No. 61/783,277, filed on Mar. 14, 2013.

(51) Int. Cl.
*A61N 1/36* (2006.01)

(52) U.S. Cl.
CPC ....... *A61N 1/36007* (2013.01); *A61N 1/36135* (2013.01); *A61N 1/36167* (2013.01)

(58) Field of Classification Search
CPC ........... A61N 1/0551; A61N 1/36007; A61N 1/36146; A61N 1/36167
See application file for complete search history.

(56) References Cited

U.S. PATENT DOCUMENTS

| | | |
|---|---|---|
| 7,054,689 B1 | 5/2006 | Whitehurst et al. |
| 7,142,925 B1 | 11/2006 | Bhadra et al. |
| 8,214,048 B1 | 7/2012 | Whitehurst et al. |
| 8,229,565 B2 | 7/2012 | Kim et al. |
| 8,644,941 B2 | 2/2014 | Rooney et al. |
| 2006/0149333 A1* | 7/2006 | Tanagho ............ A61N 1/36071 607/41 |

FOREIGN PATENT DOCUMENTS

WO WO2006-135791 12/2006

OTHER PUBLICATIONS

Yakovlev et al., "Treatment of Urinary Voiding Dysfunction Syndromes with Spinal Cord Stimulation", *Clinical Medicine & Research*, Mar. 1, 2010, vol. 8, No. 1, 22-24.

* cited by examiner

*Primary Examiner* — Joseph Dietrich
(74) *Attorney, Agent, or Firm* — Shumaker & Sieffert, P.A.

(57) ABSTRACT

In some examples, relatively low frequency (e.g., less than about 50 Hertz) electrical stimulation therapy is delivered to a target tissue site proximate to one or more of the T9, T10, T11, T12, L1, L2, or L3 ("T9-L3") spinal nerves of a patient to manage a pelvic floor disorder, such as urinary retention, fecal retention, or both. The relatively low frequency electrical stimulation therapy is configured to excite the one or more of the T9-L3 spinal nerves, which may generate an activating response from the patient related to voiding and help promote voiding by the patient. For example, the low frequency electrical stimulation may be configured to help improve the patient's pelvic sensations, which may help the patient better control urination.

33 Claims, 6 Drawing Sheets

LOW FREQUENCY ELECTRICAL STIMULATION THERAPY FOR PELVIC FLOOR DISORDERS

This application claims the benefit of U.S. Provisional Application Ser. No. 61/783,277 by Su et al., which was filed on Mar. 14, 2013, and is entitled "LOW FREQUENCY ELECTRICAL STIMULATION THERAPY FOR URINARY RETENTION." U.S. Provisional Application Ser. No. 61/783,277 by Su et al. is incorporated herein by reference in its entirety.

TECHNICAL FIELD

The disclosure relates to therapy delivery by a medical device, and, more particularly, delivery of electrical stimulation therapy.

BACKGROUND

In some cases, a pelvic floor disorder may include a dysfunction related to urinary voiding or fecal voiding. For example, one type of pelvic floor disorder, bladder dysfunction, can include overactive bladder, urgency, urinary incontinence, or urinary retention. Pelvic floor disorders may afflict people of all ages, genders, and races, and may be associated with aging, injury or illness. A variety of patient conditions may compromise performance of muscles, nerves, organs, and/or conduits within the pelvic floor, which may contribute to the pelvic floor disorder. For example, the muscles, nerves, organs, and/or conduits within the pelvic floor that cooperate to provide urinary function, e.g., to collect, store and release urine, may become dysfunctional due to injury or aging, which may result in one or more of an overactive bladder, urgency, urinary incontinence, or urinary retention.

SUMMARY

In general, the disclosure is directed to electrical stimulation therapy to manage a pelvic floor disorder, such as urinary retention, fecal retention, constipation, or any combination thereof. In some examples, relatively low frequency (e.g., less than about 50 Hertz (Hz)) electrical stimulation therapy is delivered to a target tissue site proximate to one or more of the T9, T10, T11, T12, L1, L2, or L3 ("T9-L3") spinal nerves to generate an activating response from the patient related to voiding and to promote voiding. The electrical stimulation may, for example, activate one or more nerves innervating the pelvic region of the patient (e.g., the bladder), which may help promote voiding (e.g., urination, defecation, or both). For example, the low frequency electrical stimulation may be configured to help improve the patient's pelvic sensations, which may help the patient better control urination. In some examples, a therapy system is configured to deliver relatively low frequency electrical stimulation that excites one or more of the T9-L3 spinal nerves in order to decrease the interval between bladder contractions (referred to herein as an "intercontraction interval"), decrease a micturition pressure threshold at which the patient feels the urge to void, or both.

In one aspect, the disclosure is directed to a method that comprises, with a processor, controlling a stimulation generator to deliver electrical stimulation to one or more tissue sites proximate to one or more of a T9 spinal nerve, a T10 spinal nerve, a T11 spinal nerve, a T12 spinal nerve, a L1 spinal nerve, a L2 spinal nerve, or a L3 spinal nerve of a patient to generate an activating response related to voiding.

In another aspect, the disclosure is directed to a system comprising a stimulation generator configured to generate and deliver electrical stimulation to a patient, and a processor configured to control the stimulation generator to deliver electrical stimulation to one or more tissue sites proximate to one or more of a T9 spinal nerve, a T10 spinal nerve, a T11 spinal nerve, a T12 spinal nerve, a L1 spinal nerve, a L2 spinal nerve, or a L3 spinal nerve of a patient to generate an activating response related to voiding.

In a further aspect, the disclosure is directed to a system that comprises means for generating and delivering electrical stimulation, and means for controlling means for generating and delivering electrical stimulation to deliver electrical stimulation to one or more tissue sites proximate to one or more of a T9 spinal nerve, a T10 spinal nerve, a T11 spinal nerve, a T12 spinal nerve, a L1 spinal nerve, a L2 spinal nerve, or a L3 spinal nerve of a patient to generate an activating response related to voiding.

In an additional aspect, the disclosure is directed to a computer-readable storage medium comprising instructions that, when executed by a processor, cause the processor to control a stimulation generator to deliver electrical stimulation to one or more tissue sites proximate to one or more of a T9 spinal nerve, a T10 spinal nerve, a T11 spinal nerve, a T12 spinal nerve, a L1 spinal nerve, a L2 spinal nerve, or a L3 spinal nerve of a patient to generate an activating response related to voiding.

In another aspect, the disclosure is directed to a computer-readable storage medium, which may be an article of manufacture. The computer-readable storage medium includes computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. In some examples, the computer-readable storage medium may be non-transitory.

The details of one or more example are set forth in the accompanying drawings and the description below. Other features, objects, and advantages will be apparent from the description and drawings, and from the claims.

DETAILED DESCRIPTION

Figure 1:
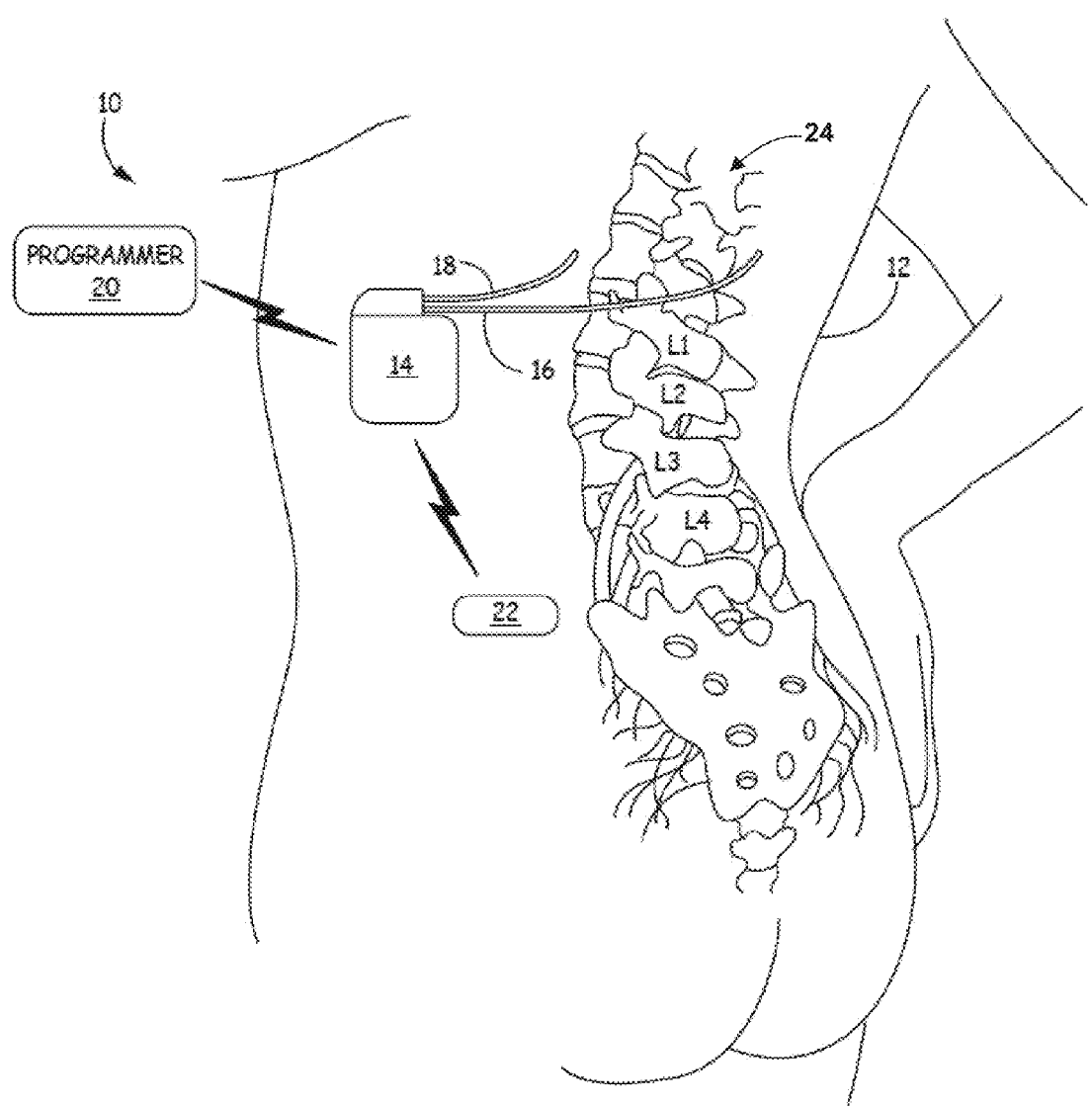
FIG. 1 is a conceptual diagram of an example therapy system that delivers a relatively low frequency electrical stimulation signal to a target tissue site proximate one or more of the T9-L3 spinal nerves, where the electrical stimulation is configured to generate an activating response from the patient related to voiding.

The devices, systems, and techniques described herein may be useful for managing one or more pelvic floor disorders, such as, but not limited to, urinary retention (other disorders characterized by hyporesponsiveness of the bladder), fecal retention, constipation (which may also include fecal voiding), and conditions related to at least one of urinary retention, fecal retention, or constipation. As described in further detail below, the electrical stimulation therapy described herein may help manage a pelvic floor disorder by increasing excitement of one or more of the T9-L3 spinal nerves, which may elicit an activating response (e.g., an excitatory response) from the patient related to voiding. Due to the target tissue site, the electrical stimulation therapy may be referred to as thoracic lumbar nerve stimulation. In the case of urinary retention, the electrical stimulation therapy may help promote urination, help a patient better control urination, or both, which may eliminate the need for the patient to be catheterized, or defecation, or both, in order to treat urinary retention. In this way, the activating response may activate one or more physiological mechanisms that help activate voiding by the patient. While urinary retention is primarily referred to herein, the devices, systems, and techniques can also be used to manage one or more other pelvic floor disorder, such as fecal retention or constipation in addition to, or instead of, urinary retention.

Bladder dysfunction is a type of pelvic floor disorder, and refers to a condition of improper functioning of the bladder or urinary tract, and may include, for example, an overactive bladder, urgency, urinary retention (also referred to as "urinary retention disorder" or "ischuria" in some cases), or urinary incontinence. Urgency is a sudden, compelling urge to urinate, and may often, though not always, be associated with urinary incontinence. Urinary incontinence refers to a condition of involuntary voiding events (i.e., involuntary loss of urine in the case of urinary incontinence), and may include urge incontinence, stress incontinence, or both stress and urge incontinence.

Urinary retention is an impaired ability of a patient to urinate, and can be characterized by the inability or impaired ability of the patient to spontaneously and controllably urinate. Non-obstructive urinary retention may be caused by include a weak bladder muscle and nerve problems that interfere with signals between the brain of the patient and the bladder. Non-obstructive urinary retention may result from one or more patient conditions, such as, but not limited to, nerve dysfunction or damage (e.g., due to stroke or vaginal childbirth, medication, spinal cord injury, stroke, tethered spinal cord syndrome, or neurogenic bladder), reduced pelvic sensations (e.g., due to diabetes), hypertonicity of the pelvic floor, dyssynergia of the bladder (or bowels in the case of fecal retention or constipation) or an abnormality in the urethral sphincter (e.g. Fowler's syndrome), or other pelvic floor musculature. For example, a patient may suffer from an inability to relax the sphincter to relax to allow urine to be passed normally. There may not be a specific neurological disorder associated with this condition.

Obstructive urinary retention may be caused by an obstruction (e.g., an obstruction of the urethra or bladder output) that prevents urine from flowing freely through the urinary tract. Obstructive urinary retention may result from one or more patient conditions, such as cancer, kidney or bladder stones, or benign prostatic hyperplasia. Obstructive fecal retention may be caused by an obstruction, such as a bowel obstruction.

Symptoms of urinary retention may include one or more of difficulty starting to urinate, difficulty fully emptying the bladder, a weak dribble or stream of urine during urination, an inability to feel when bladder is full, increased abdominal pressure, a lack of urge to urinate, strained efforts to push urine out of the bladder, frequent urination, and nocturia (e.g., waking up more than two times during sleep to urinate).

Electrical stimulation therapy described herein may help manage one or more symptoms of urinary retention or another pelvic floor disorder in which an activating respond from the patient related to voiding may be therapeutic. For example, the electrical stimulation therapy may help a patient better control urination and improve the ability of the patient to void, such as by increasing the patient's sensation to urinate. In some examples described herein, relatively low frequency electrical stimulation therapy is delivered to a target tissue site proximate one or more of the T9, T10, T11, T12, L1, L2, or L3 ("T9-L3") spinal nerves to help manage urinary retention (or fecal retention or constipation). The one or more target tissue sites may be, for example, proximate a dorsal root or ganglia of the one or more of the T9-L3 spinal nerves. In one example, the target nerve includes the hypogastric nerve. The relatively low frequency electrical stimulation may have a frequency of less than about 50 Hertz (Hz), such as about 1 Hz to about 49 Hz (e.g., 1 Hz to 49 Hz), or about 1 Hz to about 45 Hz (e.g., 1 Hz to 45 Hz).

Based on experimental results, e.g., discussed below with respect to FIGS. 6-8, it is believed that relatively low frequency (e.g., less than about 50 Hz) electrical stimulation to modulate activity of one or more of the T9-L3 spinal nerves may increase excitement (e.g., neural activity) of the one or more of the T9-L3 spinal nerves, which may help improve the ability of the patient to void and, therefore, help manage urinary retention. For example, the relatively low frequency electrical stimulation that excites one or more of the T9-L3 spinal nerves may decrease the interval between bladder contractions (referred to herein as an "intercontraction interval"). In this way, the relatively low frequency electrical stimulation that excites one or more of the T9-L3 spinal nerves may heighten the patient's sensations to void, which may help promote urination. In addition, or instead, the relatively low frequency electrical stimulation that excites one or more of the T9-L3 spinal nerves may promote urination by at least one of increasing the rate of urine flow during voiding, increasing the volume of urine voided during a voiding event (e.g., improving the extent to which the bladder is emptied during voiding), or decreasing a bladder pressure threshold at which the patient feels the urge to void (also referred to herein as a "micturition pressure threshold").

FIG. 1 is a conceptual diagram that illustrates an example of a therapy system 10 that is configured to deliver relatively low frequency electrical stimulation therapy to patient 12 to manage urinary retention, or another a pelvic floor disorder, of patient 12. As described in further detail below, in some examples, therapy system 10 delivers relatively low frequency (e.g., less than about 50 Hz) electrical stimulation to a target tissue site proximate one or more of the T9-L3 spinal nerves to modulate activity of the one or more of the T9-L3 spinal nerves to treat urinary retention. The target tissue sites may be, for example, proximate a dorsal root or ganglia of the one or more of the T9-L3 spinal nerves. Although urinary retention is primarily referred to throughout the description of FIG. 1, as well as the other figures, in other examples, therapy system 10 is configured to deliver relatively low frequency electrical stimulation to a target tissue site proximate one or more of the T9-L3 spinal nerves to help manage fecal retention or another pelvic floor disorder.

Therapy system 10 includes an implantable medical device (IMD) 14, which is coupled to leads 16, 18. System 10 also includes an external programmer 20, which communicates with IMD 14 via a wireless communication protocol, and sensor 22 (which may also be referred to as sensing module 22), which is configured to generate a signal indicative of a physiological parameter of patient 12. In some examples in which therapy system 10 is configured to manage bladder dysfunction, the physiological parameter is indicative of a condition of patient 12 related to bladder dysfunction, e.g., relating to a bladder fill level or contraction of the bladder of patient 12.

IMD 14 generally operates as a therapy device that delivers electrical stimulation therapy to patient 12 by generating and delivering a programmable electrical stimulation signal (e.g., in the form of electrical pulses or a continuous waveform) to target therapy sites proximate electrodes of leads 16, 18. In the example shown in FIG. 1, the electrodes of each lead 16, 18 are disposed proximate to a distal end of the respective lead 16, 18. The target tissue sites can be, for example, proximate one or more of the T9-L3 spinal nerves, such that electrical stimulation to the target tissue site modulates activity of the one or more of the T9-L3 spinal nerves. The T9-L3 spinal nerves may be a part of the bladder sympathetic afferent pathways. Based on the data shown in FIGS. 6-8, it is believed that relatively low frequency electrical stimulation to modulate activity of one or more of the T9-L3 spinal nerves may help elicit an activating response form patient 12 related to voiding that promotes urination by patient 12. For example, the relatively low frequency electrical stimulation that modulates one or more of the T9-L3 spinal nerves may help decrease the intercontraction interval of the bladder of patient 12, decrease a micturition pressure threshold of patient, increase the volume of urine voided during a voiding event, or any combination thereof.

FIG. 1 illustrates system 10, which is configured to deliver electrical stimulation therapy to patient 12 to manage retention. System 10 includes IMD 14, medical leads 26, 18, medical device programmer 20, and sensor 22 (which may also be referred to sensing module). FIG. 1 also illustrates a simplified anatomical view of the locations of the T9-L3 vertebrae of the vertebral column of patient 12, which corresponds to the T9-L3 spinal nerves, respectively, as well as the positioning of IMD 14 and leads 16, 18 such that electrodes (not shown in FIG. 1) of leads 16, 18 are located proximate one or more of the T9-L3 spinal nerves. In the example shown in FIG. 1, leads 16, 18 are positioned to provide bilateral stimulation to patient 12. In other examples, electrodes 30, 32 of leads 16, 18, respectively, can be positioned to deliver electrical stimulation to tissue sites proximate other ones of the T9-L3 spinal nerves, and/or to provide unilateral stimulation.

In the example shown in FIG. 1, leads 16, 18 are cylindrical. Electrodes 30, 32 of leads 16, 18, respectively, may be ring electrodes, segmented electrodes, partial ring electrodes or any suitable electrode configuration. Segmented and partial ring electrodes each extend along an arc less than 360 degrees (e.g., 90-120 degrees) around the outer perimeter of the respective lead 16, 18. In some examples, segmented electrodes may be useful for targeting different fibers of the same or different nerves to generate different physiological effects. In other examples, one or more of leads 16, 18 may be, at least in part, paddle-shaped (i.e., a "paddle" lead), and may include an array of electrodes on a common surface, which may or may not be substantially flat.

In some examples, one or more of electrodes 30, 32 may be cuff electrodes that are configured to extend at least partially around a nerve (e.g., extend axially around an outer surface of a nerve). Delivering stimulation via one or more cuff electrodes and/or segmented electrodes may help achieve a more uniform electrical field or activation field distribution relative to the nerve, which may help minimize discomfort to patient 12 that results from the delivery of electrical stimulation therapy. An electrical field may define the volume of tissue that is affected when the electrodes 30, 32 are activated. An activation field represents the neurons that will be activated by the electrical field in the neural tissue proximate to the activated electrodes.

The one or more target tissue sites proximate to one or more of the T9-L3 spinal nerves at which electrodes 30, 32 are positioned to deliver electrical stimulation can be selected based on one or more considerations, such as the particular patient 12 receiving the electrical stimulation therapy. In some examples, the target tissue sites can be identified prior to implantation of leads 16, 18. For example, a device, such as an introducer or needle, can be introduced into patient 12 and a test electrical signal can be delivered to tissue of patient 12 via the device. The device may be moved within patient 12 until a desirable physiological response is elicited by the test electrical signal, which can indicate that the device (e.g., the one or more electrodes used to deliver the test stimulation) is positioned at a tissue site that captures the target spinal nerve. In some examples, the physiological response may be detected through a motor response that may be visually detected, a sensory response as reported by the patient, or through an electrical response (e.g., sensed nerve signals). Electrodes of leads 16, 18 can subsequently be positioned at the tissue site at which the test electrical signal elicited the desirable physiological response. In other examples, the test stimulation may be delivered via leads 16, 18.

IMD 14 may be surgically implanted in patient 12 at any suitable location within patient 12, such as in the side of the lower abdomen or the side of the lower back or upper buttocks. IMD 14 can include a biocompatible outer housing, which may be formed from titanium, stainless steel, a liquid crystal polymer, or the like. One or more medical leads, e.g., leads 16, 18, may be connected to IMD 14 and surgically or percutaneously tunneled to place one or more electrodes of the respective lead at a target tissue site proximate to one or more of the T9-L3 spinal nerves. The proximal ends of leads 16, 18 are both electrically and mechanically coupled to IMD 14 either directly or indirectly, e.g., via respective lead extensions.

Electrical conductors disposed within the lead bodies of leads 16, 18 electrically connect electrodes of the respective lead to a therapy delivery module (e.g., a stimulation generator) of IMD 14. In addition, in some examples, the electrical conductors of leads 16, 18 electrically connect the electrodes of the respective lead to a sensing module of IMD 14, which enables IMD 14 to sense a physiological parameter of patient 12 via the electrodes.

A midline of patient 12 divides a body of patient 12 into two lateral sides, which can be referred to as a left side and a right side. Spinal cord 24 of patient 12 is approximately positioned at the midline of patient 12, such that one lateral side of patient 12 may be considered to be on one side of spinal cord 24 and the other lateral side of patient 12 may be considered to be on other side of spinal cord 24. Spinal nerves T9-L3 each comprise left and right branches (or portions) on respective lateral sides of patient 12. In the example shown in FIG. 1, leads 16, 18 are positioned to deliver stimulation to target tissue sites on respective lateral sides of patient 12, such that therapy system 10 is configured to deliver bilateral electrical stimulation to patient 12 via electrodes of leads 16, 18. In this way, IMD 14 may deliver bilateral electrical stimulation to patient 12 by delivering stimulation to target tissue sites on opposite sides of the midline of patient 12 via electrodes positioned on respective lateral sides of patient 12. For example, IMD 14 may deliver stimulation to a first lateral side of patient 12 via a first set of electrodes positioned on the first lateral side of patient (e.g., proximate a nerve or nerve branch on the first lateral side) and deliver stimulation to a second lateral side of patient 12 via a second set of electrodes (different than the first set) positioned on the second lateral side of patient (e.g., proximate a nerve or nerve branch on the second lateral side). In some examples, the target tissue sites are selected such that delivery of stimulation to the target tissue sites either at different times or substantially simultaneously provides an activating physiological response related to voiding of patient 12.

Leads 16, 18 can be positioned to deliver stimulation to target tissue sites proximate branches of the same nerve or branches of different nerves. For example, IMD 14 can deliver bilateral stimulation to patient 12 by delivering electrical stimulation to both the left and right nerve branches (or portions) of the same nerve and/or by delivering stimulation to a left branch of a first nerve and a right branch of a second nerve that is different than the first nerve. In addition, IMD 14 can deliver bilateral stimulation to patient 12 via a subset of electrodes of both leads 16, 18, e.g., electrodes of each lead 16, 18 can be positioned on a different lateral side of patient 12 or one or both of the leads 16, 18 can be positioned such that electrodes of the respective lead are located on both lateral sides of patient 12.

In other examples, system 10 is configured to deliver unilateral electrical stimulation to patient 12, i.e., only on one side of the midline of patient 12. In these examples, IMD 14 may only be coupled to one lead 16, 18, although both leads 16, 18 or more than two leads may also be used to provide unilateral electrical stimulation in other examples.

In some examples, the intensity of relatively low frequency electrical stimulation that is delivered to the tissue site proximate to one or more of the T9-L3 spinal nerves of patient 12 can be lower than, substantially equal to, or greater than a threshold stimulation intensity level (also referred to herein as a "threshold intensity" or "threshold intensity level") for patient 12. For example, the relatively low frequency electrical stimulation can have an intensity of about 20% to about three times the threshold stimulation intensity level of patient 12.

The threshold stimulation intensity level may be the stimulation intensity level at which an acute, physiologically significant response (also referred to herein as a threshold physiological response) of patient 12 is first observed when increasing the stimulation intensity from a low intensity to a higher intensity. Stated another way, the threshold stimulation intensity level may be defined as approximately the lowest stimulation intensity level that elicits an acute, physiologically significant response of patient 12, which may be indicative of electrical capture of a nerve. The acute, physiologically significant response may or may not be perceived by patient 12. In some examples, an acute response may be defined as a physiological response that occurs within about 30 seconds (e.g., about 10 seconds) of patient 12 receiving the stimulation.

The sufficiency of the electrical stimulation in producing an acute physiological response and/or desired therapeutic effect may be a function of stimulation intensity and time for which stimulation is delivered. Stimulation intensity may be, in turn, a function of one or more parameters. In the case of stimulation pulses, stimulation intensity may be a function of current or voltage pulse amplitude, pulse rate, and pulse width. The desired therapeutic effect is different from the acute physiological response. As one illustration, the desired therapeutic effect may be an increase in bladder contraction frequency, whereas the acute physiological response may be a motor function caused by the electrical stimulation.

The physiologically significant response used to determine the threshold intensity level can be any suitable physiological response, which may be selected by, e.g., patient 12 or a clinician. The physiological response of interest may be, for example, a patient perception (e.g., the threshold intensity level may be a patient perception threshold), a motor response (e.g., the threshold intensity level may be a motor threshold), a response indicative of capture of a nerve (e.g., the threshold intensity level may be a nerve capture threshold). The nerve capture can be detected using any suitable technique, such as, e.g., sensing afferent or efferent nerve signals via electrodes implanted in patient 12 or external to patient 12 when the stimulation is delivered to patient 12. Other types of physiological responses may be detected and may be unrelated to the type of therapy for which therapy system 10 delivers therapy in some examples. For example, a toe twitch may be considered to be a physiological response that is indicative of threshold stimulation intensity level, but the toe twitch may be a response that does not provide efficacious therapy to patient 12.

In other examples, the physiological response may be related to the type of therapy for which therapy system 10 delivers therapy. For example, the physiological response may be an acute decrease in intercontraction interval (e.g., an increase in bladder contraction frequency). The threshold intensity level, however, may not be the same as a therapy threshold, e.g., a stimulation intensity at which IMD 14 provides efficacious therapy to patient 12 to manage the patient condition (e.g., to decrease the intercontraction interval, lower the micturition pressure threshold, and/or increase the voided volume).

Whether or not a physiological response is considered to be physiologically significant can be determined by patient 12, a clinician, or another suitable person or device. As an example, the stimulation may elicit movement of a toe of patient 12, and patient 12 may define the movement of the toe as physiologically significant when the movement of the toe is perceptible or when the movement of the toe is above some arbitrary amount defined by patient 12 or the clinician.

In some examples, IMD 14 delivers the electrical stimulation therapy to patient 12 in an open loop manner, in which IMD 14 delivers the electrical stimulation therapy without intervention from a user or a sensor. For example, IMD 14 can deliver the electrical stimulation therapy substantially continuously, or periodically, e.g., according to a predetermined schedule. IMD 14 may deliver a substantially continuous (e.g., continuous or nearly continuous) relatively low frequency stimulation to one or more target tissue sites proximate one or more of the T9-T12 spinal nerves, which may be useful to treat a patient with reduced sensation in the pelvic region.

In other examples, IMD 14 delivers the electrical stimulation therapy in a closed loop manner. For example, IMD 14 may deliver the electrical stimulation therapy in response to detecting a trigger event, which can be, for example, a physiological condition (e.g., a threshold bladder pressure level or bladder volume) that indicates therapy to promote urination (e.g., to increase in the bladder contraction frequency or lower the micturition pressure threshold) may be desirable in order to help patient 12 better perceive the current bladder condition and better control urination. In some examples, the trigger event can include, for example, a detection of a particular physiological condition of patient 12 (e.g., detection of a threshold bladder pressure level or bladder volume that is indicative of an increased need for patient 12 to void), input from the patient (or a patient caretaker), or expiration of a timer comprising a predetermined duration of time. Any one or more of the trigger events may be implemented by IMD 14 alone or in combination to control the timing of the electrical stimulation therapy.

In examples in which the trigger event comprises a physiological condition of patient 12, IMD 14 may detect the physiological condition based on a physiological parameter of patient 12 sensed by, e.g., via sensor 22 or a sensing module of IMD 14. IMD 14 may detect the physiological condition based on any suitable physiological parameter such as, but not limited to, bladder impedance, bladder pressure, or any combination thereof. Thus, sensor 22 may include, for example, a pressure sensor (e.g., a strain gauge) positioned in patient 12 to detect changes in bladder pressure, electrodes for sensing bladder impedance, or any combination thereof. Example sensors that may be used are described in U.S. Pat. No. 7,769,460 to Gerber, which is entitled, "TRANSMEMBRANE SENSING DEVICE FOR SENSING BLADDER CONDITION," issued on Aug. 3, 2010, and is incorporated herein by reference in its entirety.

In some examples, IMD 14 can be configured to determine a bladder volume (also referred to herein as a fill level) based on an impedance through the bladder of patient 12, which can also vary as a function of the contraction of the bladder. An example technique that may be used, e.g., by a processor of IMD 14, programmer 20, or another device), to determine an impedance of the bladder is described in commonly assigned U.S. Patent Application Publication No. 2007/0100387 by Gerber, which published on May 3, 2007, is entitled, "IMPEDANCE-BASED BLADDER SENSING," and is incorporated herein by reference in its entirety. As described by U.S. Patent Application Publication No. 2007/0100387 by Gerber, the impedance may be measured between at least two electrodes positioned at different locations on the bladder.

As shown in FIG. 1, in some examples, sensor 22 can be physically separate from IMD 14 and can wirelessly transmit signals to IMD 14. Alternatively, sensor 22 may be carried on one of leads 16, 18 or an additional lead coupled to IMD 14.

In some examples, IMD 14 initiates the delivery of the relatively low frequency electrical stimulation therapy to patient 12 based on a time of day, which can be predetermined and stored by IMD 14, programmer 20, or another device. The time of day at which IMD 14 initiates the delivery of the electrical stimulation therapy can be, for example, associated with a time of day at which patient 12 is expected to void, e.g., based on historical data. As another example, IMD 14 may initiate the delivery of the electrical stimulation therapy when patient 12 is awake and suspend the delivery of the electrical stimulation therapy when patient 12 is sleeping. A sleep state of patient 12 can be detected by IMD 14 using, for example, patient input, a physiological parameter indicative of sleep and sensed by IMD 14 or sensor 22 or a motion sensor (e.g., an accelerometer), or the sleep times can be associated with predetermined times of day in some examples. In other examples, the times of day at which IMD 14 initiates the delivery of the electrical stimulation therapy may be selected to be at regular or irregular time intervals.

Another trigger event for initiating the delivery of the electrical stimulation therapy can be the expiration of a timer. The timer used to trigger the electrical stimulation therapy can be based on, for example, the bladder fill cycle of patient 12. In these examples, IMD 14 can restart the timer upon receiving an indication that the bladder fill cycle of patient 12 has been restarted, e.g. restarted by occurrence of a voiding event, which can be voluntary, but, in some cases, involuntary. At the beginning of a bladder fill cycle, the bladder of patient 12 is substantially empty or low, and fills throughout the cycle. The bladder fill cycle restarts upon emptying of the bladder. The duration of the timer may be selected such that IMD 14 delivers the electrical stimulation therapy when the bladder fill level of patient 12 is approximated to be at a level at which voiding by patient 12 is desirable, or at least a level at which increasing the patient's sensation to void may be desirable to promote voluntary urination by patient 12. For example, the duration of the timer may be about 50% to about 75% of the way through the bladder fill cycle for patient 12, although other durations can be used and can depend upon the severity of the patient's bladder dysfunction.

The bladder fill cycle that is used to select the timer duration can be specific to patient 12 or based on a plurality of patients, e.g., with similar bladder dysfunction disorders. In some examples, the duration of the timer is selected based on the mean, median, or shortest bladder fill cycle duration of patient 12 during a certain period of time (e.g., on the order of hours, days, or weeks), which can be prior to any delivery of stimulation to patient 12, or a time period immediately preceding the time at which the timer duration is selected.

In some examples of the closed loop therapy, instead of or in addition to a trigger event detected based on input from sensor 22 or expiration of a timer, the trigger event can include patient input. Thus, IMD 14 may deliver the electrical stimulation therapy in response to receiving patient input. For example, patient 12 can interact with programmer 20 to provide input that causes IMD 14 to deliver the electrical stimulation therapy. In this way, patient 12 may control delivery of the electrical stimulation therapy in some examples. For example, patient 12 may interact with programmer 20 to initiate the delivery of the electrical stimulation therapy in response to determining therapy to promote voluntary urination. In some cases, patient 12 may provide input that causes IMD 14 to deliver the electrical stimulation therapy in response to determining it has been a certain minimum or maximum period of time since patient 12 last voided. In this way, therapy system 10 may, in some examples, provide patient 12 with direct control of the bladder dysfunction therapy.

Programmer 20 is a device configured to communicate with IMD 14, and can be, for example, a key fob or a wrist watch, handheld computing device, computer workstation, or networked computing device. Programmer 20 includes a user interface that receives input from a user (e.g., patient 12, a patient caretaker or a clinician). In some examples, the user interface includes, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 20 can additionally or alternatively include a peripheral pointing device, such as a mouse, via which a user may interact with the user interface. In some examples, a display of programmer 20 may include a touch screen display, and a user may interact with programmer 20 via the display. It should be noted that the user may also interact with programmer 20 and/or ICD 16 remotely via a networked computing device.

A user, such as a physician, technician, surgeon, electrophysiologist, or other clinician, may also interact with programmer 20 or another separate programmer (not shown), such as a clinician programmer, to communicate with IMD 14. Such a user may interact with a programmer to retrieve physiological or diagnostic information from IMD 14. The user may also interact with programmer 20 to program IMD 14, e.g., select values for the electrical stimulation parameter values with which IMD 14 generates and delivers stimulation and/or the other operational parameters of IMD 14. For example, the user may use programmer 20 to retrieve information from IMD 14 regarding voiding events of patient 12. As another example, the user may use a programmer to retrieve information from IMD 14 regarding the performance or integrity of IMD 14 or other components of system 10, such as leads 16, 18, or a power source of IMD 14. In some examples, this information may be presented to the user as an alert if a system condition that may affect the efficacy of therapy is detected.

In some examples, patient 12 may interact with programmer 20 to control IMD 14 to deliver the electrical stimulation therapy, to manually abort the delivery of the electrical stimulation therapy by IMD 14 (e.g., while IMD 14 is delivering the stimulation therapy or is about to deliver the stimulation therapy), or to inhibit the delivery of electrical stimulation therapy by IMD 14.

In addition to or instead of interacting with programmer 20 to control therapy delivery, in some examples, patient 12 may interact directly with IMD 14 to control IMD 14 to deliver the electrical stimulation therapy, manually abort the delivery of the electrical stimulation therapy, or inhibit the delivery of the stimulation therapy. For example, a motion sensor can be integrated into or on a housing of IMD 14, and the motion sensor can generate a signal that is indicative of patient 12 tapping IMD 14 through the skin. The number, rate, or pattern of taps may be associated with the different programming capabilities, and IMD 14 may identify the tapping by patient 12 to determine when patient input is received.

In some examples, programmer 20 provides a notification to patient 12 when the electrical stimulation therapy is being delivered or notify patient 12 of the prospective delivery of the stimulation therapy to provide patient 12 with the opportunity to manually abort the electrical stimulation therapy. In such examples, programmer 20 may display a visible message, emit an audible alert signal or provide a somatosensory alert (e.g., by causing a housing of programmer 20 to vibrate). After generating the notification, programmer 20 may wait for input from patient 12 prior to delivering the electrical stimulation therapy. Patient 12 may enter input that either confirms delivery of the stimulation therapy is permitted or desirable, or manually aborts the prospective delivery of the stimulation therapy. In the event that no input is received within a particular range of time, programmer 20 may, for example, wirelessly transmit a signal that indicates the absence of patient input to IMD 14. IMD 14 may then elect to deliver or not to deliver the stimulation therapy based on the programming of IMD 14.

In some examples, programmer 20 may also be configured to generate a notification that instructs patient 12 to void. Programmer 20 can time the notification using, for example, a timer and a patient specific bladder fill cycle time or a bladder fill cycle time that is determined based on a plurality of patients.

IMD 14 and programmer 20 may communicate via wireless communication using any techniques known in the art. Examples of communication techniques may include, for example, low frequency or radiofrequency (RF) telemetry, but other techniques are also contemplated. In some examples, programmer 20 may include a programming head that may be placed proximate to the patient's body near the IMD 14 implant site in order to improve the quality or security of communication between IMD 14 and programmer 20.

System 10 shown in FIG. 1 is merely one example of a therapy system that is configured to deliver relatively low electrical stimulation therapy to modulate activity of one or more of the T9-L3 spinal nerves. Systems with other configurations of leads, electrodes, and sensors are possible. For example, in other implementations, IMD 14 may be coupled to additional leads or lead segments having one or more electrodes positioned at different locations proximate the spinal cord or in the pelvic region of patient 12. The additional leads may be used for delivering different stimulation therapies to respective stimulation sites within patient 12 or for monitoring at least one physiological parameter of patient 12.

Additionally, in other examples, a system may include more than one IMD. For example, a system may include two IMDs coupled to respective one or more leads. Each IMD can deliver stimulation to a respective lateral side of patient 12 in some examples. In addition, sensor 22 can be external to patient 12 or incorporated into a common housing as IMD 14 in some examples, and multiple sensors can be used to sense a physiological parameter of patient 12.

As another example configuration, a therapy system can include one or more microstimulators in addition to IMD 14 and leads 16, 18. The microstimulators can have a smaller form factor than IMD 14 and may not be coupled to any separate leads. Rather, the microstimulators can be leadless and configured to generate and deliver electrical stimulation therapy to patient 12 via one or more electrodes on an outer housing of the microstimulators. The microstimulators can be implanted at various locations within the pelvic floor and at different target tissue sites within patient 12, which are selected such that one or more microstimulators can deliver stimulation therapy to target tissue sites on different lateral sides of patient 12. IMD 14 or another microstimulator may act as a "master" module that coordinates the delivery of stimulation to patient 12 via the plurality of microstimulators.

System 10 may be used to treat both male and female patients.

In some examples, therapy system 10 is configured to deliver therapy to manage one or more patient conditions in addition to urinary retention (or fecal retention or constipation), such as one or more other patient conditions related to bladder dysfunction or another pelvic floor disorder. In some patients, urinary retention may coexist with one more other bladder dysfunctions or other pelvic floor disorders. Thus, it may be useful to configure IMD 14 or, in some examples, another IMD (e.g., an IMD configured to deliver electrical stimulation via one or more leads, or a leadless IMD) to deliver electrical stimulation therapy to another target tissue site in patient 12 in addition to the one or more target tissue sites to modulate activity of one or more of the T9-L3 spinal nerves.

For example, IMD 14 may also be configured to deliver electrical stimulation to manage one or more of overactive bladder, urgency, urinary incontinence, or fecal incontinence of patient 12. As an example, IMD 14 may be electrically connected to another lead that is implanted in patient 12 such that the electrodes are positioned to deliver of electrical stimulation to a target tissue site proximate any one or more of a spinal nerve, a sacral nerve, a pudendal nerve, dorsal genital nerve, a tibial nerve, an inferior rectal nerve, a perineal nerve, or branches of any of the aforementioned nerves to modulate the nerve activities to manage one or more of overactive bladder, urgency, urinary incontinence, or fecal incontinence of patient 12. For example, IMD 14 may deliver electrical stimulation to modulate the activity of the sacral and/or pudendal nerve (or branches thereof) may help reduce bladder contraction frequency, which can mitigate urgency.

Other patient conditions can include, for example, pain, sexual dysfunction, obesity, gastroparesis, muscle stimulation (e.g., functional electrical stimulation (FES) of muscles) or obesity. In this manner, in some examples, system 10 may also be configured to deliver spinal cord stimulation, peripheral nerve stimulation (PNS), peripheral nerve field stimulation (PNFS), DBS, cortical stimulation (CS), pelvic floor stimulation, gastric stimulation, or any other electrical stimulation therapy in addition to the electrical stimulation therapy for retention described herein.

Figure 2:
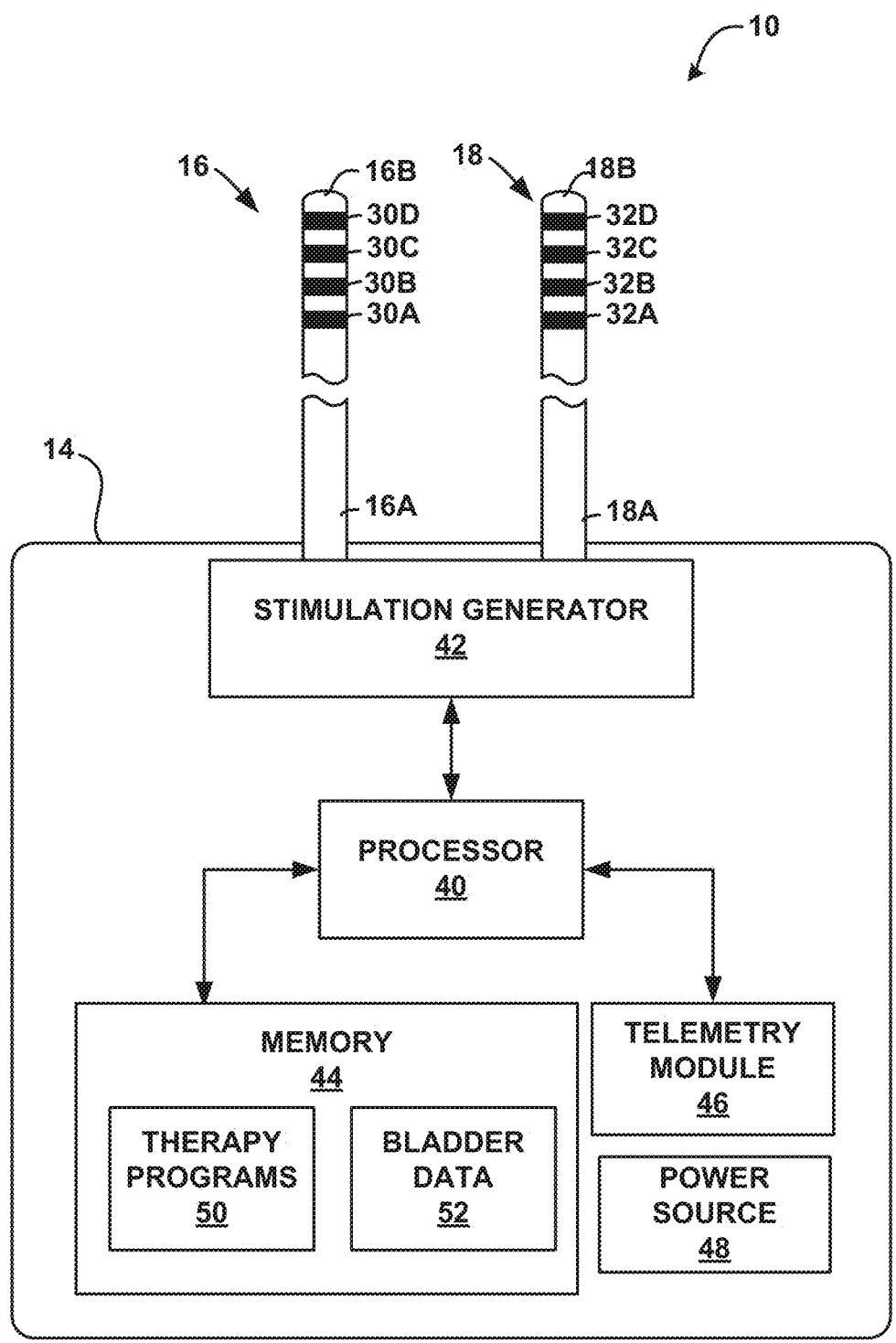
FIG. 2 is a block diagram illustrating an example configuration of an implantable medical device (IMD), which may be utilized in the system shown in FIG. 1.

FIG. 2 is a block diagram illustrating example components of IMD 14. In the example of FIG. 2, IMD 14 includes processor 40, stimulation generator 42, memory 44, telemetry module 46, and power source 48. In other examples, IMD 14 may include a fewer or greater number of components. For example, in some examples, sensor 22 can be a part of IMD 14 and substantially enclosed within the same outer housing as stimulation generator 42.

In the example shown in FIG. 2, leads 16, 18 are electrically coupled to stimulation generator 42, such that stimulation generator 42 can deliver electrical stimulation signals to patient 12 via any subset of electrodes 30A-30D (collectively referred to as "electrodes 30") of lead 16 and electrodes 32A-32D (collectively referred to as "electrodes 32") of lead 18. A proximal end 16A, 18A of each lead 16, 18, respectively, extends from the housing of IMD 14 and a distal end 16B, 18B of each lead 16, 18, respectively, is placed such that the electrodes 30, 32, respectively, are positioned to deliver electrical stimulation to a target therapy site. The target tissue sites can be, for example, proximate one or more of the T9-L3 spinal nerves.

In general, IMD 14 comprises any suitable arrangement of hardware, alone or in combination with software and/or firmware, to perform the techniques attributed to IMD 14 and processor 40, stimulation generator 42, and telemetry module 46 of IMD 14. In various examples, processor 40 can include any one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 may also include a memory 44, which include any volatile or non-volatile media, such as a random access memory (RAM), read only memory (ROM), non-volatile RAM (NVRAM), electrically erasable programmable ROM (EEPROM), flash memory, and the like. Although processor 40, stimulation generator 42, and telemetry module 46 are described as separate modules, in some examples, processor 40, stimulation generator 42, and telemetry module 46 can be functionally integrated. In some examples, processor 40, stimulation generator 42, telemetry module 46 correspond to individual hardware units, such as ASICs, DSPs, FPGAs, or other hardware units.

Memory 44 stores stimulation therapy programs 50 that specify electrical stimulation parameter values for the electrical stimulation therapy generated and delivered by IMD 14. In some examples, memory 44 also stores bladder data 52, which processor 40 may use for controlling the timing of the delivery of the stimulation therapy. For example, bladder data 52 can include parameters for trigger events, e.g., bladder conditions such as volume or pressure for which the delivery of the electrical stimulation therapy is desirable. Example values include threshold values or baseline values for at least one of bladder impedance or bladder pressure. As described in further detail below, the threshold values and baseline values may indicate a particular event, such as a bladder condition in which an increased sensation to void may help patient 12 better control voiding (e.g., better initiate voiding or more thoroughly empty of the bladder). Other example values that processor 40 can use to detect trigger events include a time of day or a timer duration, which, as described above with respect to FIG. 1, can be based on a bladder fill cycle of patient 12.

Bladder data 52 can also include information related to sensed bladder data (e.g., bladder impedance) of patient 12, which may be recorded for long-term storage and retrieval by a user, or used by processor 40 for adjustment of stimulation parameters, such as amplitude, pulse width, and pulse rate. Memory 44 may also store instructions for execution by processor 40, in addition to stimulation therapy programs 50 and bladder data 52. In some examples, memory 44 includes separate memories for storing instructions, electrical signal information, stimulation therapy programs, and bladder data.

Stimulation generator 42 is configured to generate and deliver electrical stimulation to tissue of patient 12 via selected electrodes 30, 32 carried by leads 16, 18, respectively. In some examples, processor 40 controls stimulation generator 42 by selectively accessing and loading at least one of stimulation therapy programs 50 from memory 44 to stimulation generator 42. In some cases, a clinician or patient 12 may select a particular one of stimulation therapy programs 50 from a list using a programming device, such as programmer 20 or a clinician programmer. Processor 40 may receive the selection via telemetry module 46. In some examples, stimulation generator 42 can include at least two independently controllable stimulation channels, which can, for example, permit stimulation generator 42 to independently control the delivery of electrical stimulation to two different target tissue sites, e.g., target tissue sites on both lateral sides of patient 12 can. In other examples, stimulation generator 42 can include one stimulation channel.

Stimulation generator 42 generates and delivers stimulation therapy, i.e., electrical stimulation, according to a set of electrical stimulation parameter values. In some examples, stimulation generator 42 delivers therapy in the form of electrical pulses. In such examples, relevant stimulation parameters may include a voltage amplitude, a current amplitude, a frequency (e.g., pulse rate), a pulse width, a duty cycle, or the combination of electrodes 30, 32 with which stimulation generator 42 delivers the electrical stimulation signals to tissue of patient 12. In other examples, stimulation generator 42 delivers electrical stimulation in the form of continuous waveforms. In such examples, relevant stimulation parameters may include a voltage amplitude, a current amplitude, a frequency, a shape of the stimulation signal, a duty cycle of the stimulation signal, or the combination of electrodes 30, 32 with which stimulation generator 42 delivers the electrical stimulation signals to tissue of patient 12.

In some examples, the electrical stimulation parameter values for at least some of the stimulation programs 50 may be selected to activate one or more of the T9-L3 spinal nerves, e.g., to promote urination, such as by improving the patient's perception of the bladder fill level. For example, the stimulation parameter values may be selected to increase a bladder contraction frequency, decrease a micturition pressure threshold at which patient 12 perceives the urge to void, increase the voided volume, or any combination thereof. An example range of stimulation parameter values for the stimulation therapy that may be effective in treating urinary retention (or fecal retention), e.g., when applied to the one or more of the T9-L3 spinal nerves, are as follows:

1. Frequency or pulse rate: less than about 50 Hz, such as between about 0.1 Hertz (Hz) and about 49 Hz, or between about 1 Hz to about 45 Hz, or between about 1 Hz to about 25 Hz.
2. Amplitude: between about 0.1 volts and about 50 volts, such as between about 0.5 volts and about 20 volts, or between about 1 volt and about 10 volts. For some patients, the threshold intensity level may be at an amplitude level less than or equal to about 2 volts to about 4 volts, though this may differ between patients. For current controlled systems, the amplitude may be between about 0.1 milliamps (mA) and about 50 mA, such as between about 0.5 mA and about 20 mA, or between about 1 mA and about 10 mA.
3. Pulse Width: between about 100 microseconds (μs) and about 400 μs.

The stimulation parameter values for the electrical stimulation therapy can be selected (automatically by processor 40, programmer 20, or another device, or manually by a clinician), e.g., from the parameter values listed above, such that the electrical stimulation therapy elicits, from patient 12, an activating physiological response related to voiding. In some examples, the activating physiological response related to voiding include an increase in a bladder contraction frequency, an increase in voided volume for a single voiding event, and a decrease in micturition pressure threshold, which is the bladder pressure at which a micturition response (e.g., voiding event) is activated by patient 12.

Stimulation generator 42 may generate the stimulation signals for the relatively low frequency electrical stimulation therapy based on one stimulation therapy program 50. As discussed above, in some examples, stimulation generator 42 generates and delivers the electrical stimulation therapy in an open loop manner. For example, at least some of electrical stimulation therapy programs 50 may define value for a therapy cycle, in which first time period, during which stimulation generator 42 delivers an electrical stimulation signal to patient 12, and a second time period, during which no stimulation is delivered, alternate. As another example, processor 40 can control stimulation generator 42 to generate and substantially continuously deliver electrical stimulation to patient 12.

In other examples, stimulation generator 42 delivers the electrical stimulation therapy to patient 12 in a closed loop manner (e.g., true closed-loop manner or a pseudo-closed loop manner). In examples in which stimulation generator 42 generates and delivers the electrical stimulation therapy in a closed loop manner, bladder data 52 stores at least one parameter for controlling the closed loop therapy delivery. Example parameters include one or more of a threshold bladder pressure or change in bladder pressure, a threshold impedance value, and a timer.

As described below with respect to FIG. 4, in an example closed loop stimulation therapy, processor 40 controls stimulation generator 42 to deliver electrical stimulation to patient 12 in response to detecting a trigger event, e.g., a physiological parameter of patient 12 sensed by at least one of sensor 22 or a subset of electrodes 30, 32 of leads 16, 18, expiration of a timer, and/or input from the patient (or a patient caretaker). For example, processor 40 may control stimulation generator 42 to deliver electrical stimulation to patient 12 in response to detecting a bladder volume or a bladder pressure level greater than or equal to a predetermined threshold value. In these examples, bladder data 52 can include one or more predetermined threshold values for detecting the particular bladder volume or bladder pressure level, one or more timers, or any combination thereof for controlling the electrical stimulation therapy.

One example of a trigger event is a bladder volume greater than or equal to a threshold bladder volume. As a volume of the patient's bladder increases, so may the desirability of electrical stimulation therapy to promote voluntary urination by patient 12. A bladder volume can be determined based on, for example, an impedance of a pathway through the bladder. In some examples, processor 40 is configured to determine the bladder volume based on an impedance of a path through the bladder, which may be determined based on an output generated by sensor 22 or based on an impedance sensed via a subset of electrodes 30, 32 of leads 16, 18, electrodes of a different lead electrically coupled to IMD 14, electrodes on an outer housing of IMD 14, or any other suitable electrodes. As the bladder fills, the impedance of a path through the bladder may decrease. Thus, in some examples, processor 40 is configured to control stimulation generator 42 to deliver electrical stimulation in response to determining a determined impedance of the bladder (e.g., a path through the bladder) is less than or equal to a threshold impedance value.

Another example of a trigger event is a bladder pressure greater than or equal to a threshold value. In some examples, sensor 22 includes a pressure sensor and processor 40 is configured to determine the relative bladder volume (e.g., relative to a baseline condition in which the bladder is known to be in a relatively empty state) based on a sensed bladder pressure value or a change in bladder pressure indicated by the pressure sensor. Thus, in some examples, bladder data 52 includes a threshold pressure value or a pressure change that is indicative of a bladder fullness level at which low frequency electrical stimulation to activate one or more T9-L3 spinal nerves of patient 12 may help improve the patient's pelvic sensations and promote urination, may be desirable. Processor 40 may determine a pressure value or change in pressure based on signals received from sensor 22, compare the determined pressure value or change in pressure (e.g., relative to a baseline pressure value associated with a relatively low bladder fullness level) to a threshold value stored in bladder data 52, and control stimulation generator 42 to deliver the relatively low frequency electrical stimulation therapy to one or more target tissue sites proximate to one or more of the T9-L3 spinal nerves of patient 12 in response to determining the pressure value or change in pressure is greater than or equal to the threshold value.

In examples in which processor 40 controls the delivery of the relatively low frequency electrical stimulation therapy based on a time of day, bladder data 52 can store the one or more times of day at which processor 40 initiates the delivery of the electrical stimulation therapy. Processor 40 can include a clock that tracks the time of day.

In examples in which a timer is used by processor 40 to control the timing of the delivery of the electrical stimulation therapy, bladder data 52 can store the duration of the timer. As discussed above with respect to FIG. 1, in some examples, the duration of the timer is based on the bladder fill cycle of patient 12. In some examples, processor 40 selects the duration of the timer and stores it as bladder data 52, or a clinician can select the duration of the timer and transmit the duration to IMD 14 (e.g., via programmer 20) for storage as bladder data 52.

Other trigger events, such as other the trigger events that indicate a desirability for patient 12 to voluntarily void relatively soon, a desirability for patient 12 to feel the sensation to void, or a desirability to promote voiding (e.g., by more fully emptying the bladder) are contemplated. Moreover, any of the trigger events described herein can be used in any suitable combination to time the delivery of the relatively low frequency electrical stimulation therapy to promote urination.

Closed loop therapy may allow processor 40 and stimulation generator 42 to deliver efficacious therapy to patient 12 by timing the delivery of stimulation to respond to a specific physiological state (e.g., a particular bladder fullness level) of patient 12. For example, closed loop therapy may enable processor 40 to control stimulation generator 42 to generate and deliver electrical stimulation to patient 12 to help promote urination by patient 12 at an appropriate time, e.g., when the bladder of patient 12 is at a fullness level at which a voluntary voiding event may be desirable.

The threshold values (also referred to as threshold levels) stored in memory 44 as bladder data 52 may be determined using any suitable technique. In some examples, the threshold values may be determined during implantation of IMD 14 or during a trial period following implant of IMD 14. In some examples, the trigger event threshold values, times of day, or timer durations may be adapted over time based on user input, e.g., via external programmer 20. As an example, patient 12 may indicate, via programmer 20, when a voluntary voiding event takes place. When the patient input is received, processor 40 may determine a bladder impedance value or pressure value immediately prior to the event based in signals received from sensor 22. A new trigger event threshold value may be determined using this impedance value or pressure value.

In some examples of the closed loop therapy or pseudo-closed loop therapy, processor 40 controls stimulation generator 42 to initiated delivery of the electrical stimulation therapy and continue delivering the electrical stimulation for a predetermined therapy period, the duration of which may be stored in memory 44 and/or a memory of another device (e.g., programmer 20). The therapy period may be, for example, approximately 10 seconds to about one hour, such as about 5 minutes to about 30 minutes, although other therapy periods are contemplated. The therapy period may depend on the patient condition. The predetermined period of time can be determined by a clinician in some examples and stored in memory 44 of IMD.

In some examples, in addition to or instead of the predetermined therapy period, stimulation generator 42 delivers the relatively low frequency electrical stimulation therapy for a therapy period controlled by patient 12. In such examples, patient 12 may interact with programmer 20 to control the delivery time. As an example, stimulation generator 42 may deliver the electrical stimulation therapy as long as patient 12 presses a button on a keypad or touch screen of programmer 20. As another example, processor 40 controls stimulation generator 42 to initiate the delivery of the electrical stimulation therapy in response to receiving a first input from patient 12 (e.g., by presses a button on a keypad or touch screen of programmer (20) and controls stimulation generator 42 to terminate the delivery of the electrical stimulation therapy in response to receiving a second subsequent input from patient 12 indicating the stimulation should be terminated. In operation, processor 40 can receive the patient input via telemetry module 46 and control stimulation generator 42 to deliver therapy according to the received input, or receive the patient input more directly, e.g., via a motion sensor incorporated into IMD 14.

If processor 40 controls the duration of the therapy period of the electrical stimulation therapy based on both a predetermined period of time and the patient input, processor 40 can, for example, control stimulation generator 42 to deliver the electrical stimulation therapy for the longer of the predetermined period of time or the period of time determined based on patient input, or, in other examples, the shorter of those two periods of time.

In other examples, processor 40 controls the duration of the therapy period during which stimulation generator 42 delivers the electrical stimulation therapy based on a physiological condition of patient 12. For example, in examples in which stimulation generator 42 initiates the delivery of the electrical stimulation therapy based on a sensed patient condition, stimulation generator 42 may deliver the stimulation therapy until the condition is no longer detected. As an example, processor 40 can control stimulation generator 42 to initiate the delivery of the relatively low frequency electrical stimulation therapy in response to detecting a bladder impedance less than or equal to a predetermined trigger event threshold and continue delivering the electrical stimulation therapy until the bladder impedance is greater than the predetermined trigger event threshold. When processor 40 detects a bladder impedance that is greater than the predetermined termination threshold, processor 40 may determine that the volume of the patient's bladder has decreased (e.g., due to voluntary voiding by patient 12), such that termination of the electrical stimulation therapy configured to promote urination is appropriate. In the foregoing example, stimulation generator 42 delivers the electrical stimulation therapy until a relatively low bladder fill level of patient 12 is detected.

A relatively low bladder fill level of patient 12 that causes stimulation generator 42 to terminate delivery of the electrical stimulation therapy can be detected using other techniques. In some examples, processor 40 detects a relatively low bladder volume of patient 12 based on patient input that is provided after patient 12 voluntarily voids. Processor 40 can receive the input from an input device separate from IMD 14 (e.g., programmer 20) via telemetry module 46 or from a sensor that is coupled to processor 40 (e.g., a motion sensor that detects tapping of IMD 14 by patient 12).

Telemetry module 46 includes any suitable hardware, firmware, software or any combination thereof for communicating with another device, such as programmer 20 (FIG. 1). Processor 40 controls telemetry module 46 to exchange information with medical device programmer 20 and/or another device external to IMD 14. Under the control of processor 40, telemetry module 46 may receive downlink telemetry, e.g., patient input, from and send uplink telemetry, e.g., an alert, to programmer 20 with the aid of an antenna, which may be internal and/or external. Processor 40 may provide the data to be uplinked to programmer 20 and the control signals for the telemetry circuitry within telemetry module 46, and receive data from telemetry module 46. Processor 40 may transmit operational information and receive stimulation programs or stimulation parameter adjustments via telemetry module 46. Also, in some examples, IMD 14 may communicate with other implanted devices, such as stimulators, control devices, or sensors, via telemetry module 46.

Processor 40 monitors patient input received via telemetry module 46 and takes appropriate action. As previously described, in some examples, telemetry module 46 may receive an indication from programmer 20 that patient 12 provided input indicative of desirability of therapy to promote urination. In response to receiving the patient input via telemetry module 46, processor 40 may control stimulation generator 42 to generate and deliver relatively low frequency stimulation configured to promote urination for a predetermined amount of time or until a particular patient condition is detected or until further patient input requesting the termination of the therapy delivery is received. Patient 12 may provide such input, for example, immediately after a voiding event.

Power source 60 delivers operating power to the components of IMD 14. Power source 60 may include a battery and a power generation circuit to produce the operating power. In some examples, the battery may be rechargeable to allow extended operation.

Figure 3:
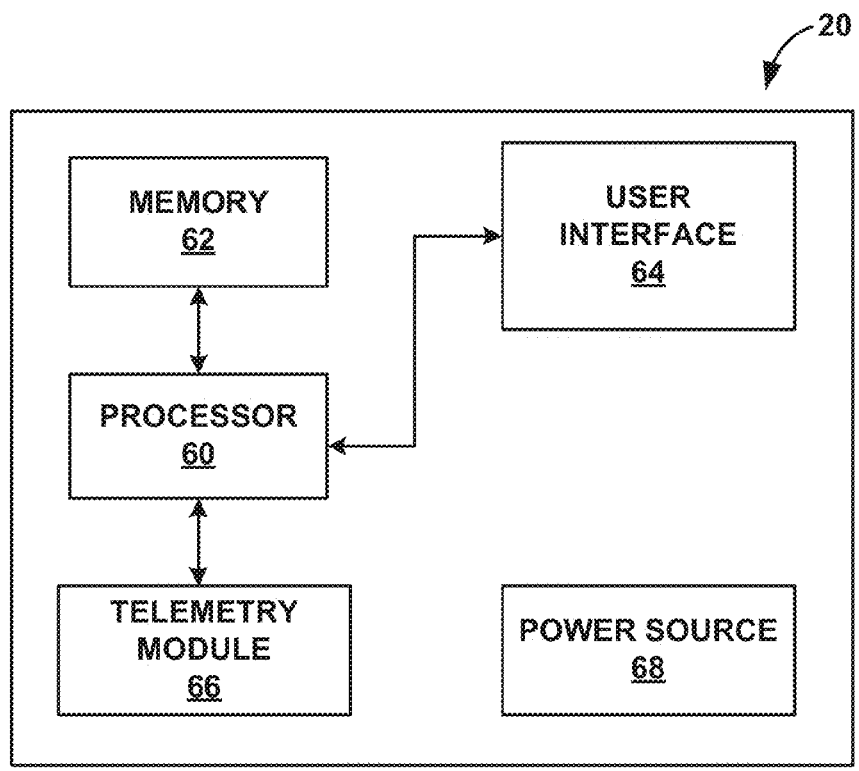
FIG. 3 is a block diagram illustrating an example configuration of an external programmer which may be utilized in the system shown in FIG. 1.

FIG. 3 is a block diagram illustrating example components of external programmer 20. While programmer 20 may generally be described as a hand-held computing device, the programmer may be a notebook computer, a cell phone, or a workstation, for example. As illustrated in FIG. 3, in some examples, external programmer 20 includes processor 60, memory 62, user interface 64, telemetry module 66, and power source 68. Memory 62 may store program instructions that, when executed by processor 60, cause processor 60 and external programmer 20 to provide the functionality ascribed to external programmer 20 throughout this disclosure.

Programmer 20 comprises any suitable arrangement of hardware, alone or in combination with software and/or firmware, to perform the techniques attributed to programmer 20, and processor 60, user interface 64, and telemetry module 66 of programmer 20. In various examples, processor 60 may include one or more processors, such as one or more microprocessors, DSPs, ASICs, FPGAs, or any other equivalent integrated or discrete logic circuitry, as well as any combinations of such components. Programmer 20 also, in various examples, may include a memory 62, such as RAM, ROM, PROM, EPROM, EEPROM, flash memory, a hard disk, a CD-ROM, a floppy disk, a cassette, magnetic media, or optical media comprising executable instructions for causing the one or more processors to perform the actions attributed to them. Moreover, although processor 60 and telemetry module 66 are described as separate modules, in some examples, processor 60 and telemetry module 66 are functionally integrated.

Memory 62 may store program instructions that, when executed by processor 60, cause processor 60 and programmer 20 to provide the functionality ascribed to programmer 20 throughout this disclosure. In some examples, memory 62 may further include therapy information, e.g., therapy programs defining the electrical stimulation therapy, similar to those programs 50 (FIG. 3) stored in memory 44 of IMD 14, and bladder data similar to bladder data 52 stored by IMD 14. The stimulation programs and/or bladder data 42 stored in memory 62 may be downloaded into memory 44 of IMD 14 or vice versa.

User interface 64 may include a button or keypad, lights, a speaker for voice commands, a display, such as a LCD, LED, or CRT. In some examples the display may be a touch screen. As discussed in this disclosure, processor 60 may present and receive information relating to stimulation therapy via user interface 64. For example, processor 60 may receive patient input via user interface 64. The input may be, for example, in the form of pressing a button on a keypad or selecting an icon from a touch screen.

Processor 60 may also present information to patient 12 (or a patient caretaker), such as alerts related to delivery of the stimulation therapy to patient 12 via user interface 64. Telemetry module 66 supports wireless communication between IMD 14 and programmer 20 under the control of processor 60. Telemetry module 66 may also be configured to communicate with another computing device via wireless communication techniques, or direct communication through a wired connection. Telemetry module 66 may be substantially similar to telemetry module 46 described above, providing wireless communication via an RF or proximal inductive medium. In some examples, telemetry module 66 may include an antenna, which may take on a variety of forms, such as an internal or external antenna. Examples of local wireless communication techniques that may be employed to facilitate communication between programmer 20 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 20 without needing to establish a secure wireless connection.

Although not shown, programmer 20 may additionally or alternatively include a data or network interface to another computing device, to facilitate communication with the other device, and presentation of information relating to electrical stimulation therapy via the other device. The other computing device can be, for example, a remote computing device (e.g., at a clinic) or a cloud computing device.

IMD 14, programmer 20, or both, may control of the timing of the delivery of the electrical configured to elicit an activating response that promotes urination by patient 12. If external programmer 20 controls the stimulation, programmer 20 may transmit therapy programs for implementation by processor 40 to IMD 14. Alternatively, programmer 20 may transmit a signal to IMD 14 indicating that processor 40 should execute locally stored programs or therapy routines. In such a manner, control over the electrical stimulation may be distributed between IMD 14 and external programmer 20, or may reside in either one alone.

In one example, patient 12 may control the electrical stimulation therapy delivered by IMD 14 via programmer 20. For example, patient 12 may initiate and/or terminate delivery of the stimulation therapy by IMD 14 via user interface 64. In this way, patient 12 may use programmer 20 to deliver the stimulation therapy "on demand," such as when patient 12 determines that that it may be an appropriate time to void or when patient 12 is intending on voiding. The electrical stimulation may improve the ability of the patient to void, such as by decreasing the micturition threshold or by increasing the voided volume.

Power source 68 delivers operating power to the components of programmer 20. Power source 68 may include a battery and a power generation circuit to produce the operating power. In some examples, the battery may be rechargeable to allow extended operation.

As discussed above, in some examples, IMD 14 delivers relatively low frequency (e.g., less than about 50 Hz) electrical stimulation to one or more target tissue sites proximate one or more of the T9-L3 spinal nerves in an open loop manner. In other examples, IMD 14 delivers the relatively low frequency electrical stimulation in a closed loop (including a pseudo-closed loop) manner.

Figure 4:
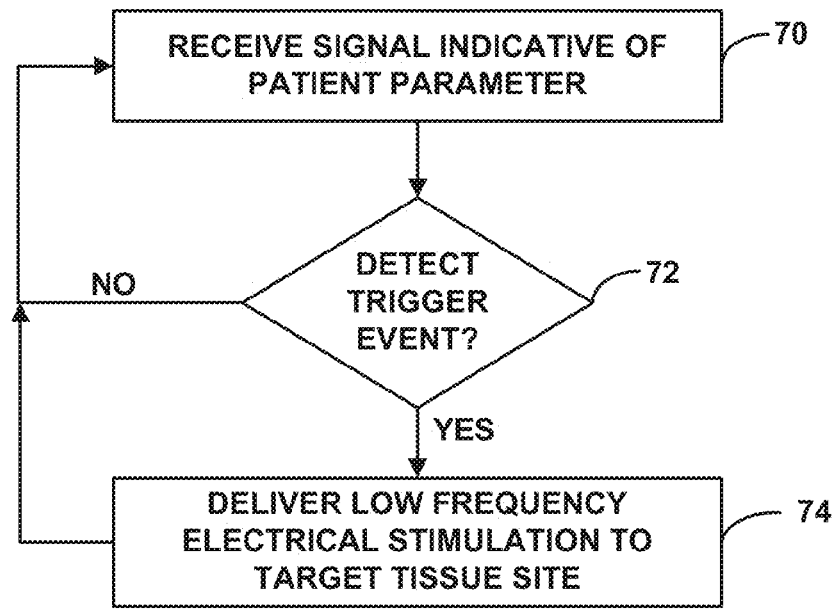
FIG. 4 is a flow diagram that illustrates an example technique for delivering electrical stimulation therapy to a patient to manage urinary retention.
Figure 5:
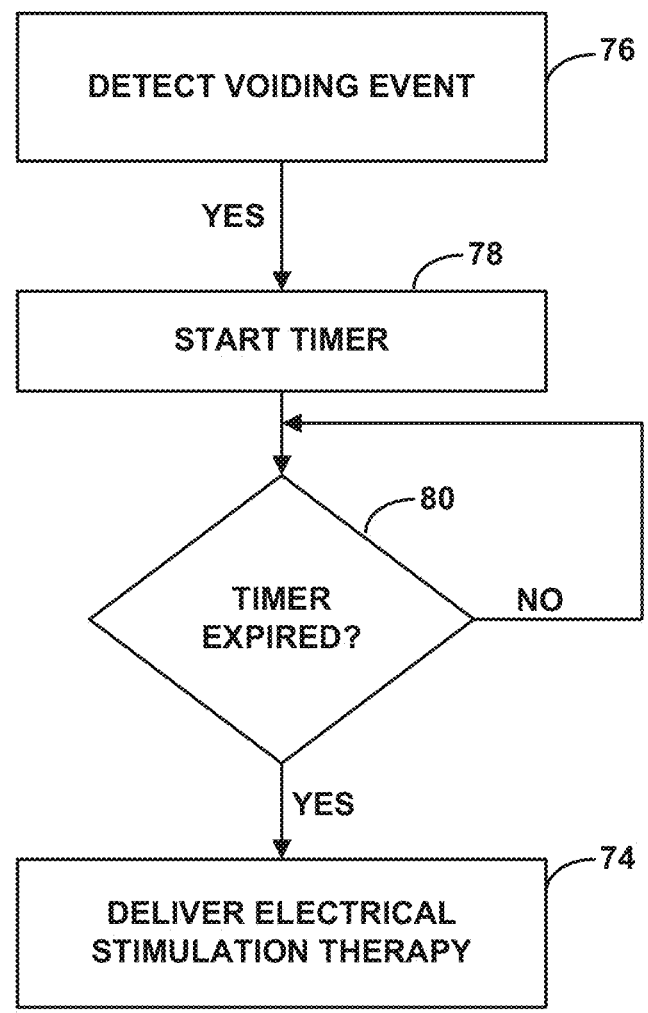
FIG. 5 is a flow diagram of another example technique for delivering electrical stimulation therapy to a patient to manage urinary retention.

FIG. 4 is a flow diagram illustrating an example closed loop or pseudo-closed loop technique implemented by a therapy system, such as therapy system 10 (FIG. 1), to deliver relatively low frequency electrical stimulation to promote urination by patient 12. While FIGS. 4 and 5 are described with respect to therapy system 10, in other examples, the techniques for providing the relatively low frequency electrical stimulation to one or more target tissue sites proximate one or more of the T9-L3 spinal nerves to generate an activating response related to voiding described herein may be implemented by other therapy systems, which may include different components or configurations than therapy system 10. In addition, while processor 40 is primarily referred to in FIGS. 4 and 5, in other examples, a processor of another device (e.g., programmer 20), alone or in combination with processor 40, can perform the techniques shown in FIG. 4.

In the technique shown in FIG. 4, processor 40 receives a signal indicative of a patient parameter (70), e.g., from sensor 22 or another sensor (e.g., a sensing module that is a part of IMD 14). Processor 40 determines whether a trigger event is detected based on the signal (72). Examples of trigger events that may be detected include, but are not limited to, a bladder pressure or change in pressure greater than or equal to a predetermined threshold value, a bladder volume greater than or equal to a predetermined threshold value, a bladder impedance less than or equal to a predetermined threshold value, or any combination thereof.

In other examples, the trigger event may be a time of day, expiration of a timer, and patient input. In examples in which processor 40 is configured to control the delivery of the electrical stimulation based on these type of trigger events, the technique shown in FIG. 4 may not include receiving the signal indicative of a patient parameter (70).

If processor 40 does not detect a trigger event ("NO" branch of block 72), then processor 40 may continue receiving the signal indicative of a patient parameter (70) and determining, based on the received signal, whether the trigger event is detected (72). On the other hand, if processor 40 detects a trigger event ("YES" branch of block 72), then processor 40 controls stimulation generator 42 to deliver the relatively low frequency electrical stimulation to one or more target tissue sites proximate one or more of the T9-L3 spinal nerves to generate an activating response related to voiding (74).

In one example, the trigger event is a bladder fill level (also referred to herein as a bladder volume) at or above a threshold fill level. The trigger event can be detected, for example, when processor 40 detects a bladder impedance value that is less than a trigger event threshold impedance value stored in memory 44 as bladder data 52 (FIG. 3). Other techniques for determining a bladder fill level are contemplated, such as based on a bladder pressure value or a change in bladder pressure value relative to a baseline that is greater than or equal to a trigger event threshold value. Any suitable technique, such as those described above, can be used to detect a bladder pressure. Processor 40 may, for example, receive a signal generated by a strain gauge sensor (which can be, for example, sensor 22) on a bladder surface.

In addition to or instead of the trigger events that are based on a sensed patient parameter, the trigger event can be patient input. Patient 12 may provide the patient input via user interface 64 of programmer 20, e.g., by activating a button on a keypad or select an icon using a touch screen of programmer 20. Programmer 20 may be configured to wirelessly communicates the patient input to IMD 14 via the respective telemetry modules 66, 46. In other examples, patient 12 may provide input indicating the delivery of the electrical stimulation therapy is desirable by directly interacting with IMD 14. For example, IMD 14 may include a motion sensor that detects movement of IMD 14 and patient 12 may provide input by tapping the skin proximate IMD 14 in a predetermined pattern, such that processor 40 detects the movement and characterizes the movement as patient input.

In another example, the trigger event is an expiration of a timer that processor 40 starts upon receiving an indication that patient 12 has voided, thereby reducing the bladder fill level. The duration of the timer can be, for example, selected to be a duration of time that is expected to pass before the bladder of patient 12 is filled to a level at which voiding may be desirable. Thus, at the expiration of the timer, the bladder of patient 12 is at a volume at which generating an activating response related to voiding may be desirable in order to promote urination, such as by enhancing pelvic floor sensations related to voiding perceived by patient 12. Processor 40 can receive an indication that patient 12 has voluntarily voided using any suitable technique, e.g., receiving input from patient 12 (or a patient caretaker) via programmer 20 or by directly interacting with IMD 14 or based on a physiological parameter sensed by IMD 14 or sensor 22 that indicates a bladder volume.

In some examples, stimulation generator 42 delivers the electrical stimulation therapy (74) for a therapy period duration controlled by patient 12. For example, patient 12 may control the duration of the therapy period for the electrical stimulation therapy by interacting with programmer 20, e.g., by pressing a button on a keypad or a touch screen to terminate the electrical stimulation therapy or set a duration of time for the electrical stimulation therapy, or by interacting directly with IMD 14 (e.g., by tapping skin superior to the implanted IMD 14). IMD 14 can be programmed with a maximum duration for the electrical stimulation therapy, such that patient 12 is provided with limited control of the duration of the electrical stimulation therapy. The maximum duration for the electrical stimulation therapy can be, for example, approximately one hour, although other durations of time are contemplated.

In addition to or instead of determining the therapy period duration based on patient input, stimulation generator 42 can deliver the electrical stimulation therapy (74) for a predetermined period of time (e.g., a therapy period) immediately following the detection of the trigger event. In some examples, the therapy period can be about 10 seconds to about one hour, such as about five minutes to 30 minutes. The duration of the predetermined period of time may be selected such that the activating physiological effect related to voiding is generated for a period of time sufficient for patient 12 to voluntarily void with the aid of the electrical stimulation therapy. After the predetermined period of time, processor 40 controls stimulation generator 42 to terminate the delivery of the electrical stimulation, and continue monitoring for the trigger event (72) based on a signal indicative of a patient parameter or based on another input. The technique shown in FIG. 4 can then be repeated as necessary.

In some examples, after stimulation generator 42 delivers the electrical stimulation therapy (74) for a predetermined period of time, processor 40 determines whether the trigger event is still present using any of the techniques described above for detecting the trigger event. For example, if the trigger event is the detection of a particular patient condition, processor 40 can determine whether the patient condition that triggered the delivery of the electrical stimulation therapy is still observed. As an example, processor 40 may determine whether the bladder impedance is still less than or equal to a trigger event threshold value. This may indicate, for example, that patient 12 has not voided yet, such that the electrical stimulation therapy to promote voiding may still be desirable. As another example, if the trigger event is patient input, processor 40 can determine whether the patient has provided additional input that indicates delivery of the electrical stimulation therapy is desirable.

If the trigger event is still detected after the delivery of the electrical stimulation therapy, then processor 40 may control stimulation generator 42 to continue delivering the electrical stimulation therapy again for another predetermined period of time. This technique may be repeated in some examples until the trigger event is no longer detected. If the trigger event is not detected after delivery of the electrical stimulation therapy for a predetermined duration of time, then processor 40 can cease delivery of the electrical stimulation therapy and continue monitoring for the trigger event (72) based on a signal indicative of a patient parameter or based on another input. The technique shown in FIG. 4 can then be repeated as necessary.

In some examples, the trigger event is the expiration of a timer. FIG. 5 is a flow diagram of a technique with which processor 40 controls stimulation generator 42 to generate and deliver the electrical stimulation therapy to patient 12 in response to detection of the expiration of a timer that has a duration that is based on voiding by patient 12. The technique shown in FIG. 5 is performed in a closed loop manner.

In the technique shown in FIG. 5, to initiate of the delivery of therapy to patient 12, processor 40 detects a voiding event (76), in which patient 12 voids and decreases the fill level of the bladder. The voiding event can be voluntary or involuntary in the example shown in FIG. 5. Processor 40 can detect voiding by patient 12 using any suitable technique. In some examples, processor 40 receives input from patient 12 (or a patient caretaker) indicating the occurrence of a voiding event. Patient 12 can provide input to programmer 20 or another external device, which may then transmit an indication of the input to processor 40, or patient 12 may interact directly with IMD 14 (e.g., by tapping skin superior to the implant site of IMD 14).

In other examples, processor 40 detects an occurrence of a voiding event based on a sensed physiological parameter of patient 12. For example, processor 40 can detect the occurrence of a voluntary voiding event based on an electromyogram (EMG) of the urinary sphincter muscle of patient 12 or another muscle that activates during voiding. Sensor 22 (FIG. 1) may generate the EMG in some examples, or processor 40 may sense the EMG of the muscle via a subset of electrodes 30, 32 of leads 16, 18 (FIG. 3). In some examples, memory 44 of IMD 14 (FIG. 3) stores an EMG template or threshold values (e.g., a signal amplitude or frequency value) that is associated with a voluntary voiding event, and processor 40 compares a sensed EMG to the stored template or threshold to detect the voluntary voiding event. For example, when a sensed EMG substantially matches the stored template, processor 40 may determine that patient 12 is purposefully activating the monitored muscle to voluntarily void. A voluntary voiding event can also be detected based on other physiological parameters, such as a bladder pressure, urinary sphincter pressure, and the like. In addition, other techniques for detecting a voluntary voiding event may be used. Similar techniques can be used to detect an involuntary voiding event.

In response to detecting a voiding event (76), processor 40 starts a timer (78). The duration of the timer is predetermined and stored in memory 44 of IMD 14 and/or a memory of another device. As discussed above, the timer duration may be based on a bladder fill cycle of patient 12, such as about 50% to about 75% of the way through the bladder fill cycle for patient 12, although other durations can be used and can depend upon the severity of the patient's bladder dysfunction. As shown in FIG. 5, in response to determining the timer expired ("YES" branch of block 80), processor 40 controls stimulation generator 42 to deliver the electrical stimulation therapy to one or more target tissue sites proximate one or more of the T9-L3 spinal nerves to generate an activating response related to voiding to promote voiding (74). In the example shown in FIG. 5, processor 40 can deliver the electrical stimulation therapy to patient 12 for any suitable duration of time, such as a predetermined amount of time or until a voiding event is detected.

The technique shown in FIG. 5 adapts the timing of the electrical stimulation therapy to the bladder fill cycle of patient 12. A bladder fill cycle begins immediately after the patient voluntarily voids. As time passes since the patient's last voluntary voiding event, the patient's bladder fills. During the beginning of the fill cycle, therapy to promote urination may not be necessary or even desirable. However, at a later point in the fill cycle, such as when the bladder reaches a fill level at which voiding may be desirable, therapy to aid voiding may be desirable to help patient 12 initiate a voiding event or more thoroughly empty the bladder during the voiding event. (e.g., therapy to aid voiding by causing the patient's bladder to contract more frequently). After patient 12 voluntarily voids, the bladder fill cycle of patient 12 restarts, such that the therapy to aid voiding may not be desirable. Thus, in some examples, after detecting another voiding event (76), processor 40 may restart the timer (78) and deliver electrical stimulation therapy (74) when the timer expires.

Using the techniques shown in FIGS. 4 and 5, IMD 14 can provide responsive stimulation to patient 12 to manage urinary retention. Delivering the electrical stimulation therapy upon detection of a trigger event, rather than on a substantially regular basis, may help reduce the patient's adaptation to the electrical stimulation therapy by limiting the amount of the electrical stimulation therapy. In addition, implementing the electrical stimulation therapy only when needed may help conserve power of power source 48 (FIG. 3) of IMD 14. Conserving power may help elongate the useful life of IMD 14.

Figure 6:
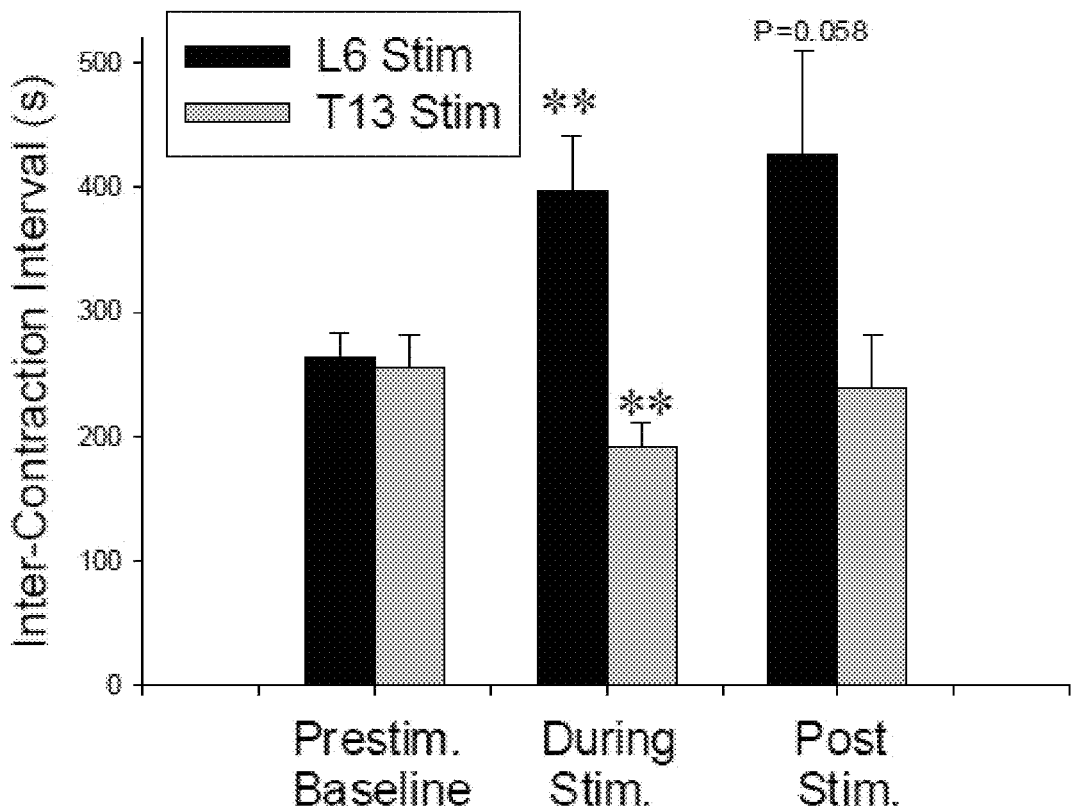
FIGS. 6-8 are bar graphs that illustrate micturition responses of rat subjects in response to electrical stimulation of the T13 and L6 spinal nerve roots
Figure 7:
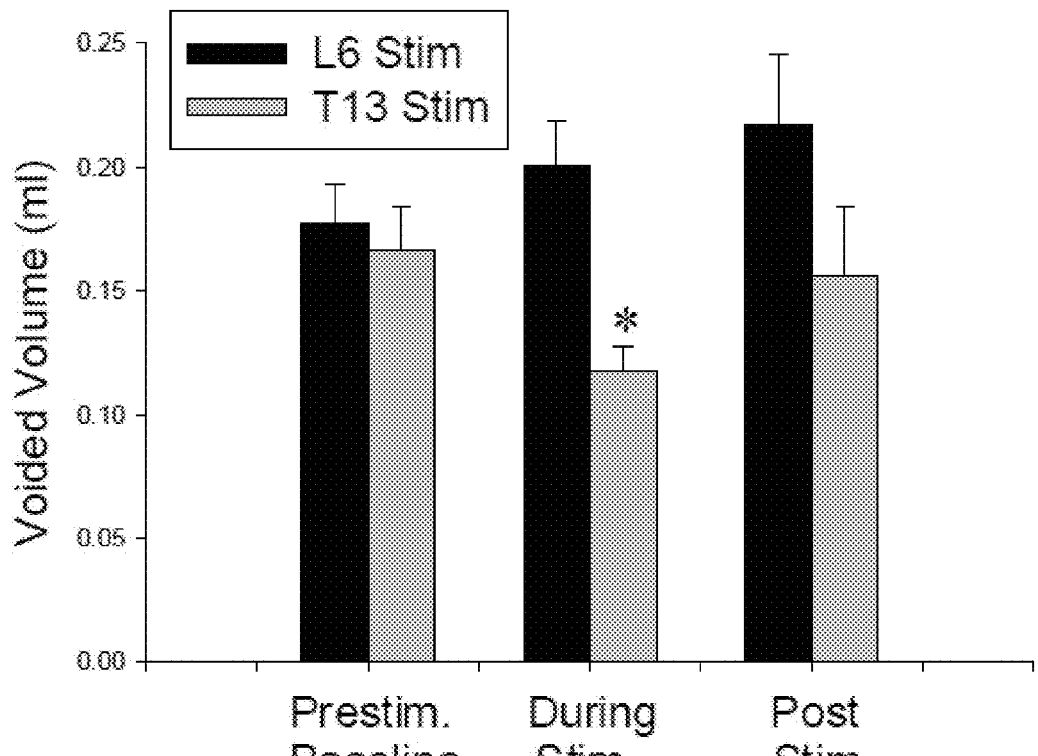
Figure 8:
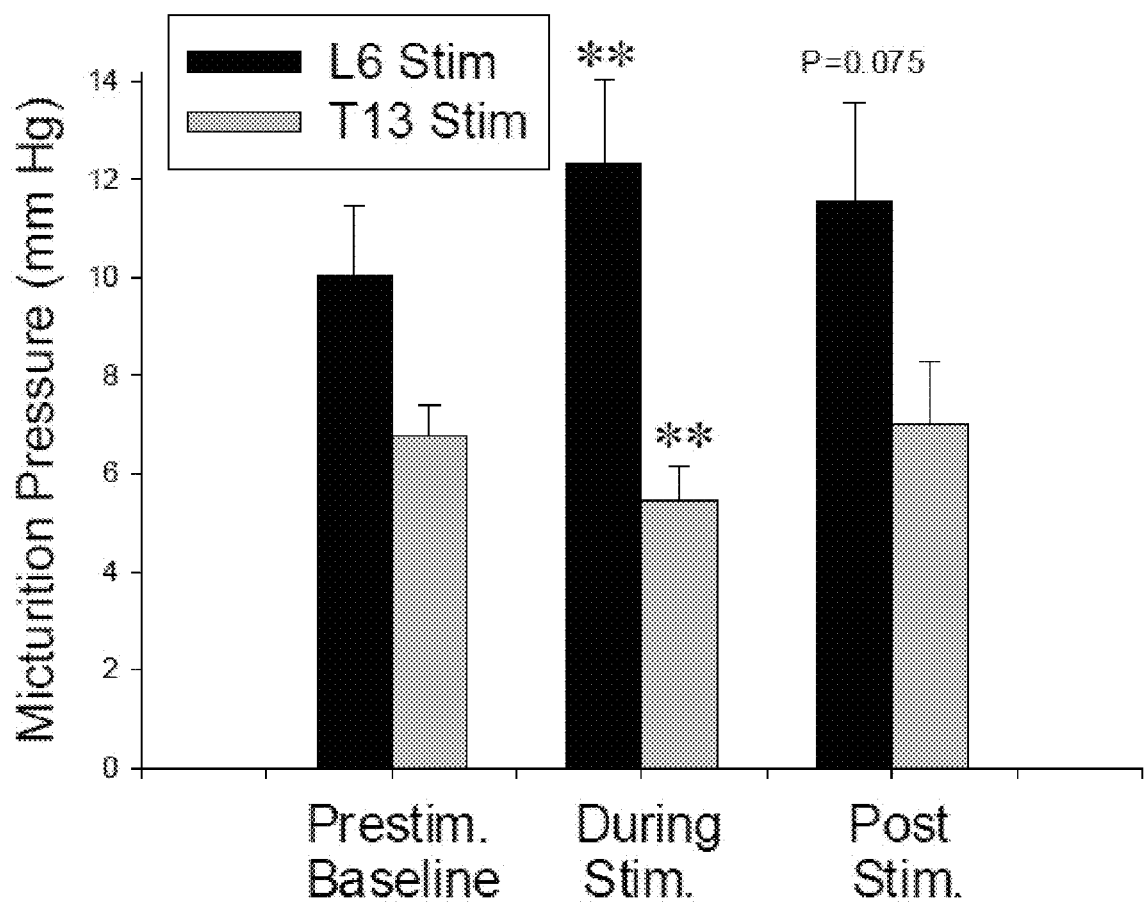

FIGS. 6-8 are bar graphs that illustrate micturition responses of rat subjects in response to electrical stimulation of the T13 and L6 spinal nerve roots. The data shown in FIGS. 6-8 was obtained from a plurality of tests performed on anesthetized (via urethane 1.2 grams per kilogram subcutaneous (gm/kg s.c.) supplemented with up to 0.5% inhaled isoflurane) female Sprague-Dawley rats weighing approximately 225 grams to about 290 grams. The bar graphs illustrate the effect of T13 and L6 spinal nerve stimulation on cystometric measures.

For each rat subject that received electrical stimulation, the neuroforaminal openings where the T13 or L6 spinal nerves exited were surgically exposed bilaterally and instrumented with monopolar stimulation electrodes bilaterally by placement of the stimulation electrode tip into the neuroforamin using polysiloxane gel to hold the electrode in contact with the nerves. Grounding electrodes were placed dorsally.

During the tests, bilateral electrical stimulation was delivered to the T13 and L6 spinal nerves via the stimulation electrodes. The electrical stimulation consisted of trains of biphasic square wave pulses delivered at three times the motor threshold of the subject for about 10 minutes. The motor threshold was determined to be the minimal current needed to evoke any observable skeletal muscle contraction in the particular rat subject. Rats with a motor threshold greater than 0.4 mA were excluded from the study. Stimulation intensities to each lateral side of a rat were adjusted independently based on the motor threshold determined for each lateral side. The electrical stimulation was delivered at a frequency of about 10 Hz and a pulse width of about 100 microseconds ($\mu$sec).

Various cystometric parameters indicative of the micturition response of each rat subject were determined. In particular, the cystometric parameters used to quantify micturition responses of the subjects included an interval of time between bladder contractions (also referred to herein as inter-contraction interval), micturition threshold pressure, and voided volume. The mean of these measures for five or more micturitions prior to electrical stimulation were compared with micturitions obtained during electrical stimulation and to five or more micturitions following electrical stimulation. An analysis of variance (ANOVA) with Tukey's honestly significant difference (HSD) post tests and Students-t tests was used to characterize the micturition responses to the electrical stimulation.

In order to simulate a bladder fill cycle to determine the parameters indicative of the micturition response of each rat subject, the bladder of each rat subject was externalized via an abdominal incision that exposed the bladder, and a flared tip PE50 polyethylene catheter was placed into the dome of the bladder and secured using a purse string suture. A continuous infusion of room temperature normal saline was then infused into the bladder at a rate of approximately 0.05 milliliters per minute (ml/min). An in-line pressure transducer was used to measure intravesical pressure, which was used to determine the pressure immediately prior to voiding, referred to herein as the micturition threshold pressure, for the particular subject. The volume of each voiding event was measured by capturing the urine in a glass tube and weighing the voided urine. A baseline measure of micturition responses for the subject was obtained for one hour prior to bilateral electrical stimulation of either the T13 or L6 nerves.

FIGS. 6-8 are bar graphs that illustrate changes in the micturition responses of the test subjects produced by the electrical stimulation. The results of the experiments shown in FIGS. 6-8 were analyzed with GraphPad Prism 4 software (available from GraphPad Software, Inc. of San Diego, Calif.). The data shown in FIGS. 6-8 was obtained based on data generated from the delivery of bilateral electrical stimulation to the T13 nerve roots of five test subjects in accordance with the techniques described above, and the delivery of bilateral electrical stimulation to the L6 nerve roots of seven test subjects in accordance with the techniques above.

FIG. 6 is a bar graph that illustrates the mean inter-contraction interval for the test subjects prior to delivery of any electrical ("Prestim. Baseline"), during the delivery of electrical stimulation ("During Stim.") and after the delivery of electrical stimulation ("Post Stim."). As shown in FIG. 6, it was found that bilateral stimulation of the T13 spinal nerve roots of the subjects produced a statistically significant shortening of the inter-contraction interval, whereas bilateral stimulation of the L6 spinal nerve roots of the subjects produced a statistically significant lengthening of ICI inter-contraction interval. In particular, for the subjects receiving the T13 nerve root stimulation, the mean baseline inter-contraction interval was about 250 seconds, whereas the mean inter-contraction interval during the delivery of electrical stimulation (i.e., during the stimulation period) was less than 200 seconds, and the mean inter-contraction interval after the stimulation period was about 240 seconds. In addition, for the subjects receiving the L6 nerve root stimulation, the mean baseline inter-contraction interval was about 275 seconds, whereas the mean inter-contraction interval during the delivery of electrical stimulation (i.e., during the stimulation period) was about 400 seconds, and the mean inter-contraction interval after the stimulation period was about 425 seconds The variance in the data shown in FIG. 6 was about $p<0.05$ for the inter-contraction intervals determined during electrical stimulation and about $p<0.058$ for inter-contraction intervals determined during the post-stimulation data.

Human patients do not have a T13 spinal nerve. However, the T9-L3 (e.g., T12-L1) spinal nerves of human patients may be anatomically similar to the T9-L3 spinal nerve of a rat subject. For example, the T12-L1 spinal nerves may innervate the pelvic region of the human patient, such as the bladder, just as the T13-L1 spinal nerve of a rat subject innervates the pelvic region of the rat subject. The pelvic nerves of a human patient may go through a plurality of segments of the spinal cord, e.g., the T9-L3 segments. Due to anatomical similarities, the delivery of electrical stimulation to one or more of the T9-L3 spinal nerves of human patients may have similar physiological effects as the delivery of electrical stimulation to the T13 spinal nerve of a rat subject.

The data shown in FIG. 6 indicates that the delivery of electrical stimulation to the T12-L3 spinal nerves of a human patient may help manage urinary retention by shortening the inter-contraction interval, and, therefore, increasing bladder activity, relative to a baseline condition in which no electrical stimulation is delivered.

FIG. 7 is a bar graph that illustrates the mean voided volume for the test subjects prior to delivery of any electrical ("Prestim. Baseline"), during the delivery of electrical stimulation ("During Stim.") and after the delivery of electrical stimulation ("Post Stim."). As shown in FIG. 7, it was found that bilateral stimulation of the T13 nerve roots of the subjects produced a statistically significant reduction of the voided volume, whereas bilateral stimulation of the L6 nerve roots of the subject produced a statistically significant increase in the voided volume relative to the baseline in which no electrical stimulation was delivered. In particular, for the subjects receiving the T13 nerve root stimulation, the mean baseline voided volume was about 0.165 milliliters, whereas the mean voided volume during the delivery of electrical stimulation (i.e., during the stimulation period) was about 0.12 milliliters, and the mean voided volume after the stimulation period was about 0.155 milliliters. In addition, for the subjects receiving the L6 nerve root stimulation, the mean voided volume was about 0.18 milliliters, whereas the mean voided volume during the delivery of electrical stimulation (i.e., during the stimulation period) was about 0.20 milliliters, and the mean voided volume after the stimulation period was about 0.22 milliliters. The variance in the data shown in FIG. 7 was about $p<0.05$ for the voided volume determined during electrical stimulation.

The rat subjects did not have a known urinary retention condition, such that the subjects did not retain a significant amount of urine after a voiding event, and the voided volume may correlate to the frequency of voiding. A larger voided volume indicates that the subject was not voiding frequently enough and was holding the urine. A smaller voided volume indicates the subject was voiding more frequently. The data shown in FIG. 7 indicates that delivery of electrical stimulation to the T13 nerve roots of the rat subjects increased the frequency of voiding. Thus, the data shown in FIG. 7 indicates that the delivery of electrical stimulation to one or more of the T12-L3 spinal nerves of a human patient may help manage urinary incontinence by helping the patient void more frequently.

FIG. 8 is a bar graph that illustrates the mean micturition pressure threshold, i.e., the pressure at which a micturition response (e.g., voiding event) was activated, for the test subjects prior to delivery of any electrical ("Prestim. Baseline"), during the delivery of electrical stimulation ("During Stim.") and after the delivery of electrical stimulation ("Post Stim."). As shown in FIG. 8, it was found that bilateral stimulation of the T13 nerve roots of the subjects produced a statistically significant reduction of the micturition pressure threshold, whereas bilateral stimulation of the L6 nerve roots of the subject produced a statistically significant increase in the micturition pressure threshold. In particular, for the subjects receiving the T13 nerve root stimulation, the mean micturition pressure threshold was about 7 mm Hg, whereas the mean micturition pressure threshold during the delivery of electrical stimulation (i.e., during the stimulation period) was about 5.5 mm Hg, and the mean micturition pressure threshold after the stimulation period was about 7 mm Hg. In addition, for the subjects receiving the L6 nerve root stimulation, the mean micturition pressure threshold was about 10 mm Hg, whereas the mean micturition pressure threshold during the delivery of electrical stimulation was greater than 12 mm Hg, and the mean micturition pressure threshold after the stimulation period was about 11.5 mm Hg.

The data shown in FIG. 8 indicates that the delivery of electrical stimulation to one or more of the T12-L1 spinal nerves of a human patient may help manage urinary incontinence by helping lower the bladder pressure at which a micturition response of the patient is activated.

The data shown in FIGS. 6-8 indicates that relatively low frequency stimulation of one of the T13 spinal nerve and the L6 spinal nerve may activate neural structures related to voiding, and may help reduce the likelihood of inadequate intensity of cystometric measures during voiding. The observation that T13 and L6 electrical stimulation had opposite effects on cystometric measures suggests a potential role for relatively low frequency stimulation of the T13 (or, in the case of human patients, T9-T12) spinal nerve in some patient conditions in which there is hyporesponsiveness of the bladder, such as in the case of urinary retention.

The techniques described in this disclosure, including those attributed to IMD 14, programmer 20, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. While the techniques described herein are primarily described as being performed by processor 40 of IMD 14 and/or processor 60 of programmer 14, any one or more parts of the techniques described herein may be implemented by a processor of one of IMD 14, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be stored on, as one or more instructions or code, a computer-readable medium and executed by a hardware-based processing unit. Computer-readable media may include computer-readable storage media forming a tangible, non-transitory medium. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:

1. A method comprising:
   with a processor, controlling a stimulation generator to deliver electrical stimulation via at least one electrode implanted at one or more tissue sites proximate to one or more of a T9 spinal nerve, a T10 spinal nerve, a T11 spinal nerve, a T12 spinal nerve, a L1 spinal nerve, a L2 spinal nerve, or a L3 spinal nerve of a patient, wherein the electrical stimulation is configured to generate an excitatory activating response of the patient that promotes voiding.

2. The method of claim 1, wherein controlling the stimulation generator to deliver the electrical stimulation comprises controlling the stimulation generator to deliver an electrical stimulation signal having a frequency of less than about 50 Hertz.

3. The method of claim 1, wherein controlling the stimulation generator to deliver the electrical stimulation comprises controlling the stimulation generator to deliver electrical stimulation having an intensity of about 20% to about three times a threshold stimulation intensity of the patient, wherein the threshold stimulation intensity is defined by a plurality of stimulation parameters and elicits a physiological response in the patient indicative of electrical capture of a nerve.

4. The method of claim 1, wherein controlling the stimulation generator to deliver the electrical stimulation comprises controlling the stimulation generator in an open loop manner.

5. The method of claim 1, further comprising detecting, with the processor, a trigger event, wherein controlling the stimulation generator to deliver the electrical stimulation comprises controlling the stimulation generator to initiate the delivery of the electrical stimulation in response to detecting the trigger event.

6. The method of claim 5, wherein detecting the trigger event comprises at least one of detecting a predetermined time of day or detecting expiration of a timer.

7. The method of claim 6, wherein detecting the trigger event comprises detecting expiration of the timer, the method further comprising:
   with the processor, detecting a voiding event of the patient; and
   with the processor, starting the timer in response to detecting the voiding event of the patient.

8. The method of claim 5, wherein detecting the trigger event comprises detecting a bladder condition indicative of a bladder volume greater than or equal to a trigger event threshold.

9. The method of claim 5, wherein detecting the trigger event comprises detecting a bladder impedance less than or equal to a trigger event threshold.

10. The method of claim 5, wherein detecting the trigger event comprises detecting a bladder pressure greater than or equal to a trigger event threshold.

11. The method of claim 5, wherein detecting the trigger event comprises detecting the trigger event based on user input.

12. The method of claim 5, wherein controlling the stimulation generator to deliver the electrical stimulation comprises:
    after detecting the trigger event, determining the trigger event is no longer detected; and
    controlling the stimulation generator to terminate the delivery of electrical stimulation in response to determining the trigger event is no longer detected.

13. The method of claim 1, wherein controlling the stimulation generator to deliver the electrical stimulation comprises controlling the stimulation generator to deliver the electrical stimulation to the patient for a predetermined period of time.

14. The method of claim 1, further comprising delivering, by the stimulation generator via the at least one electrode, the electrical stimulation to the one or more tissue sites proximate to one or more of the T9 spinal nerve, the T10 spinal nerve, the T11 spinal nerve, the T12 spinal nerve, the L1 spinal nerve, the L2 spinal nerve, or the L3 spinal nerve of the patient.

15. A system comprising:
    at least one electrode configured to be implanted at one or more tissue sites proximate to one or more of a T9 spinal nerve, a T10 spinal nerve, a T11 spinal nerve, a T12 spinal nerve, a L1 spinal nerve, a L2 spinal nerve, or a L3 spinal nerve of a patient;
    a stimulation generator configured to generate and deliver electrical stimulation to a patient; and
    a processor configured to control the stimulation generator to deliver electrical stimulation via the at least one of electrode when the at least one electrode is implanted at the one or more tissue sites, wherein the electrical stimulation is configured to generate an excitatory activating response of the patient that promotes voiding when the electrical stimulation is applied via the at least one electrode implanted at the one or more tissue sites proximate to the one or more of the T9 spinal nerve, the T10 spinal nerve, the T11 spinal nerve, the T12 spinal nerve, the L1 spinal nerve, the L2 spinal nerve, or the L3 spinal nerve of the patient.

16. The system of claim 15, wherein the electrical stimulation has a frequency of less than about 50 Hertz.

17. The system of claim 15, the electrical stimulation has an intensity of about 20% to about three times a threshold stimulation intensity of the patient, wherein the threshold stimulation intensity is defined by a plurality of stimulation parameters and elicits a physiological response in the patient indicative of electrical capture of a nerve.

18. The system of claim 15, wherein the processor is configured to control the stimulation generator to deliver the electrical stimulation to the one or more tissue sites in an open loop manner.

19. The system of claim 15, wherein the processor is configured to detect a trigger event and control the stimulation generator to deliver the electrical stimulation by at least controlling the stimulation generator to initiate the delivery of the electrical stimulation in response to detecting the trigger event.

20. The system of claim 19, wherein the processor is configured to detect the trigger event by at least one of detecting a predetermined time of day or detecting expiration of a timer.

21. The system of claim 20, wherein the processor is configured to detect the trigger event by at least detecting expiration of the timer, and wherein the processor is configured to detect a voiding event of the patient, and start the timer in response to detecting the voiding event of the patient.

22. The system of claim 19, further comprising a sensing module, wherein the processor is configured to receive a signal generated by the sensing module, and detect the trigger event by at least detecting, based on the signal, a bladder condition indicative of a bladder volume greater than or equal to a trigger event threshold.

23. The system of claim 19, further comprising a sensing module configured to generate a signal indicative of a bladder impedance of the patient, wherein the processor is configured to receive the signal generated by the sensing module, and detect the trigger event in response to determining, based on the signal, the bladder impedance of the patient is less than or equal to a trigger event threshold.

24. The system of claim 19, further comprising a sensing module configured to generate a signal indicative of a bladder pressure of the patient, wherein the processor is configured to receive the signal generated by the sensing module, and detect the trigger event in response to determining, based on the signal, the bladder pressure is greater than or equal to a trigger event threshold.

25. The system of claim 19, further comprising a user interface configured to receive user input, wherein the processor is configured to detect the trigger event by at least receiving user input via the user interface.

26. The system of claim 19, wherein, after detecting the trigger event, the processor is configured to determine the trigger event is no longer detected and control the stimulation generator to terminate the delivery of the electrical stimulation in response to determining the trigger event is no longer detected.

27. The system of claim 15, wherein the processor is configured to control the stimulation generator to deliver the electrical stimulation by at least controlling the stimulation generator to deliver the electrical stimulation to the patient for a predetermined period of time.

28. A system comprising:
means for generating and delivering electrical stimulation; and
means for controlling the means for generating and delivering electrical stimulation to deliver electrical stimulation via at least one electrode implanted at one or more tissue sites proximate to one or more of a T9 spinal nerve, a T10 spinal nerve, a T11 spinal nerve, a T12 spinal nerve, a L1 spinal nerve, a L2 spinal nerve, or a L3 spinal nerve of a patient, wherein the electrical stimulation is configured to generate an excitatory activating response of the patient that promotes voiding when the electrical stimulation is delivered to the one or more tissue sites proximate to the one or more of the T9 spinal nerve, the T10 spinal nerve, the T11 spinal nerve, the T12 spinal nerve, the L1 spinal nerve, the L2 spinal nerve, or the L3 spinal nerve of the patient.

29. The system of claim 28, wherein the electrical stimulation has a frequency of less than about 50 Hertz.

30. The system of claim 28, wherein the electrical stimulation has an intensity of about 20% to about three times a threshold stimulation intensity of the patient, wherein the threshold stimulation intensity is defined by a plurality of stimulation parameters and elicits a physiological response in the patient indicative of electrical capture of a nerve.

31. A computer-readable medium comprising instructions that, when executed by a processor, cause the processor to control a stimulation generator to deliver electrical stimulation via at least one electrode implanted at one or more tissue sites proximate to one or more of a T9 spinal nerve, a T10 spinal nerve, a T11 spinal nerve, a T12 spinal nerve, a L1 spinal nerve, a L2 spinal nerve, or a L3 spinal nerve of a patient, wherein the electrical stimulation is configured to generate an excitatory activating response of the patient that promotes voiding when the electrical stimulation is delivered to the one or more tissue sites proximate to the one or more of the T9 spinal nerve, the T10 spinal nerve, the T11 spinal nerve, the T12 spinal nerve, the L1 spinal nerve, the L2 spinal nerve, or the L3 spinal nerve of the patient.

32. The computer-readable medium of claim 31, wherein the electrical stimulation has a frequency of less than about 50 Hertz.

33. The computer-readable medium of claim 31, wherein the electrical stimulation has an intensity of about 20% to about three times a threshold stimulation intensity of the patient, wherein the threshold stimulation intensity is defined by a plurality of stimulation parameters and elicits a physiological response in the patient indicative of electrical capture of a nerve.

* * * * *

UNITED STATES PATENT AND TRADEMARK OFFICE
CERTIFICATE OF CORRECTION

PATENT NO. : 9,446,235 B2  
APPLICATION NO. : 14/210981  
DATED : September 20, 2016  
INVENTOR(S) : Su et al.

Page 1 of 1

It is certified that error appears in the above-identified patent and that said Letters Patent is hereby corrected as shown below:

In the Claims

Column 30, Line 38: "via the at least one of electrode" should read --via the at least one electrode--

Signed and Sealed this  
Eighteenth Day of September, 2018

Andrei Iancu  
*Director of the United States Patent and Trademark Office*